United States Patent
Ali et al.

(10) Patent No.: US 10,556,060 B2
(45) Date of Patent: Feb. 11, 2020

(54) DRUG DELIVERY PROGRAMMING TECHNIQUES

(71) Applicant: Medtronic, Inc., Minneapolis, MN (US)

(72) Inventors: Irfan Z. Ali, Woodbury, MN (US); Prasanna Anbazhagan, Maple Grove, MN (US); William J. Mitchell, Eden Prairie, MN (US); Earle T. Roberts, Maple Grove, MN (US); Touby A. Drew, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 77 days.

(21) Appl. No.: 15/811,215

(22) Filed: Nov. 13, 2017

(65) Prior Publication Data

US 2018/0064872 A1 Mar. 8, 2018

Related U.S. Application Data

(63) Continuation of application No. 14/537,502, filed on Nov. 10, 2014, now Pat. No. 9,814,834.
(Continued)

(51) Int. Cl.
*A61M 5/168* (2006.01)
*G06F 19/00* (2018.01)

(52) U.S. Cl.
CPC ..... *A61M 5/16877* (2013.01); *G06F 19/3468* (2013.01)

(58) Field of Classification Search
CPC .............. A61M 5/16877; G06F 19/3468
See application file for complete search history.

(56) References Cited

U.S. PATENT DOCUMENTS

| 4,925,444 A | 5/1990 | Orkin et al. |
| 8,162,888 B2 | 4/2012 | Kalpin |

(Continued)

FOREIGN PATENT DOCUMENTS

| EP | 0302752 A2 | 2/1989 |
| WO | 03082380 A1 | 10/2003 |
| WO | 2005084273 A2 | 9/2005 |

OTHER PUBLICATIONS

Baiyasi et al., "Math for Nursing and Allied Health," Teaching/Learning Center, Delta College, Jan. 2001, 21 pp.
(Continued)

*Primary Examiner* — Lauren P Farrar
(74) *Attorney, Agent, or Firm* — Shumaker & Sieffert, P.A.

(57) ABSTRACT

Devices, systems, and techniques for programming drug delivery are described. Such techniques may account for diffusion and mixing of drug within the fluid or allow for more flexible programming options. In one example, a method may include determining one or more fluid delivery parameters (e.g., volume, flow rate, or period of time) for a fluid that is a mixture of two other fluids. The determination may be based on one or more fluid delivery parameters of the two other fluids and/or a concentration profile representing the mixing between the two other fluids. In other examples, drug delivery programming may be facilitated by the selection of various patterns and steps of drug delivery. The system may track volume of delivered fluid to maintain desired dosing of the patient.

20 Claims, 14 Drawing Sheets

Related U.S. Application Data

(60) Provisional application No. 61/902,720, filed on Nov. 11, 2013.

(56) References Cited

U.S. PATENT DOCUMENTS

| | | | |
|---|---|---|---|
| 8,246,573 B2 | 8/2012 | Ali et al. | |
| 8,348,884 B2 | 1/2013 | Hildebrand et al. | |
| 8,352,043 B2 | 1/2013 | Goetz et al. | |
| 8,444,609 B2 | 5/2013 | Christenson et al. | |
| 9,314,572 B2 | 4/2016 | Morris et al. | |
| 9,814,572 B2 | 11/2017 | Edelman et al. | |
| 2003/0216682 A1 | 11/2003 | Junker | |
| 2006/0041222 A1 | 2/2006 | Dewing et al. | |
| 2006/0041223 A1 | 2/2006 | Dewing et al. | |
| 2006/0041287 A1 | 2/2006 | Dewing et al. | |
| 2006/0041288 A1 | 2/2006 | Dewing et al. | |
| 2006/0160900 A1 | 7/2006 | Hildebrand et al. | |
| 2007/0106208 A1 | 5/2007 | Uber, III et al. | |
| 2007/0197963 A1 | 8/2007 | Griffiths et al. | |
| 2007/0255236 A1 | 11/2007 | Christenson et al. | |
| 2009/0137980 A1 | 5/2009 | Ali | |
| 2009/0137987 A1 | 5/2009 | Ali | |
| 2010/0010646 A1 | 1/2010 | Drew et al. | |
| 2010/0100038 A1* | 4/2010 | Walker | A61M 5/14244 604/82 |
| 2010/0185181 A1 | 7/2010 | Alme et al. | |
| 2010/0185182 A1 | 7/2010 | Alme et al. | |
| 2010/0185183 A1 | 7/2010 | Alme et al. | |
| 2010/0274221 A1 | 10/2010 | Sigg et al. | |
| 2010/0312230 A1 | 12/2010 | Ulleslad et al. | |
| 2011/0144540 A1 | 6/2011 | Shen et al. | |
| 2011/0166522 A1 | 7/2011 | Haase et al. | |
| 2011/0257591 A1 | 10/2011 | Nelson Konen et al. | |
| 2011/0257798 A1 | 10/2011 | Ali et al. | |
| 2011/0264006 A1 | 10/2011 | Ali et al. | |
| 2011/0264034 A1 | 10/2011 | Roberts et al. | |
| 2012/0053514 A1 | 3/2012 | Robinson et al. | |
| 2012/0053562 A1 | 3/2012 | Haase | |
| 2012/0109099 A1 | 5/2012 | Rogers et al. | |
| 2012/0209241 A1 | 8/2012 | Drew | |
| 2012/0220528 A1 | 8/2012 | Van Antwerp et al. | |
| 2012/0277155 A1 | 11/2012 | Van Antwerp et al. | |
| 2012/0277716 A1 | 11/2012 | Ali et al. | |
| 2012/0277717 A1 | 11/2012 | Ali et al. | |
| 2013/0041418 A1 | 2/2013 | Rubin et al. | |

OTHER PUBLICATIONS

International Preliminary Report on Patentability from International Application No. PCT/US2014/064843, dated May 26, 2016, 9 pp.
International Search Report and Written Opinion from Counterpart International Patent Application No. PCT/US2014/064843, dated Feb. 9, 2015, 13 pp.
Prosecution History from U.S. Appl. No. 14/537,502, dated Aug. 8, 2016 through Jul. 10, 2017, 47 pp.

* cited by examiner

DRUG DELIVERY PROGRAMMING TECHNIQUES

This application is a continuation application of U.S. patent application Ser. No. 14/537,502, filed Nov. 10, 2014 and entitled "DRUG DELIVERY PROGRAMMING TECHNIQUES," which claims the benefit of U.S. Provisional Patent Application No. 61/902,720, to Ali, filed Nov. 11, 2013, and entitled "DRUG DELIVERY PROGRAMMING TECHNIQUES," both of which are incorporated herein by reference in their entirety.

TECHNICAL FIELD

The present disclosure relates to medical devices and, more particularly, programming drug delivery devices.

BACKGROUND

Implantable fluid delivery devices are used to treat a number of physiological, psychological, and emotional conditions, including chronic pain, tremor, Parkinson's disease, diabetes, epilepsy, urinary or fecal incontinence, sexual dysfunction, obesity, spasticity, or gastroparesis. For some medical conditions, an implantable fluid delivery device provides the best, and in some cases the only, therapy to restore a patient to a more healthful condition.

An implantable fluid delivery device typically provides a patient with a programmable dosage or infusion of a drug or other therapeutic agent. The fluid delivery device typically includes a reservoir for storing the therapeutic agent, a fill port, a pumping mechanism to pump the therapeutic agent from the reservoir, a catheter to transport the therapeutic agent stored in the reservoir to a patient's anatomy, and electronics to control the pumping mechanism.

SUMMARY

In general, the disclosure relates to systems and methods for programming drug delivery. In one example, drug delivery may be programmed, or controlled, for delivery transitions. The transition may include changing between different drug delivery sources (e.g., external and implanted drug pumps), changing between different concentrations of a drug, or even changing the type of one or more drugs being delivered to a patient. For example, a system may obtain delivery parameters for two different fluids to be delivered to the patient (e.g., fluids with different concentration of the same therapeutic agent). Since a mixture of the two fluids may occur at the interface between both fluids, a transition period may be used to deliver this mixture. The system may then generate delivery parameters (e.g., a flow rate and period of time) for delivering the fluid mixture during the transition period. The transition period may thus avoid overdosing and/or underdosing of the therapeutic agent by accounting for the mixture between both fluids.

In other examples, the system may facilitate the generation of flexible drug delivery schedules. The system may receive user input selecting one or more patterns that each defines a recurring time period for delivering a drug. Within each pattern, the system may receive user input selecting one or more steps that each defines a respective set of drug delivery parameters for the respective step. Each of the one or more patterns may be associated with any stored step, such that a step can be assigned to any pattern desired by a user.

In one example, the disclosure is directed to a method that includes obtaining, by one or more processors, one or more first fluid delivery parameters that at least partially define delivery of a first fluid within a downstream portion of a fluid path of a fluid delivery system, wherein a medical pump and a catheter of the fluid delivery system define at least a portion of the fluid path, obtaining, by the one or more processors, one or more second fluid delivery parameters that at least partially define delivery of a second fluid within an upstream portion of the fluid path upstream from the first fluid, wherein the second fluid comprises a therapeutic agent, determining, by the one or more processors and based on the one or more first fluid delivery parameters and the one or more second fluid delivery parameters, one or more third fluid delivery parameters that at least partially define delivery of a third fluid located between the first fluid and the second fluid in the fluid path, wherein the third fluid comprises a mixture of the first fluid and a second fluid, and wherein at least some of the one or more third fluid delivery parameters are different than the one or more first and second fluid delivery parameters, and outputting, by the one or more processors, the one or more third fluid delivery parameters for controlling the medical pump to deliver the third fluid to a patient.

In another example, the disclosure is directed to a device that includes one or more processors configured to obtain one or more first fluid delivery parameters that at least partially define delivery of a first fluid within a downstream portion of a fluid path of a fluid delivery system, wherein a medical pump and a catheter of the fluid delivery system define at least a portion of the fluid path, obtain one or more second fluid delivery parameters that at least partially define delivery of a second fluid within an upstream portion of the fluid path upstream from the first fluid, wherein the second fluid comprises a therapeutic agent, determine, based on the one or more first fluid delivery parameters and the one or more second fluid delivery parameters, one or more third fluid delivery parameters that at least partially define delivery of a third fluid located between the first fluid and the second fluid in the fluid path, wherein the third fluid comprises a mixture of the first fluid and the second fluid, and wherein at least some of the one or more third fluid delivery parameters are different than the one or more first and second fluid delivery parameters, and output the one or more third fluid delivery parameters for controlling the medical pump to deliver the third fluid to a patient.

In another example, the disclosure is directed to a system that includes means for obtaining one or more first fluid delivery parameters that at least partially define delivery of a first fluid within a downstream portion of a fluid path of a fluid delivery system, wherein a medical pump and a catheter of the fluid delivery system define at least a portion of the fluid path, means for obtaining one or more second fluid delivery parameters that at least partially define delivery of a second fluid within an upstream portion of the fluid path upstream from the first fluid, wherein the second fluid comprises a therapeutic agent, means for determining, based on the one or more first fluid delivery parameters and the one or more second fluid delivery parameters, one or more third fluid delivery parameters that at least partially define delivery of a third fluid located between the first fluid and the second fluid in the fluid path, wherein the third fluid comprises a mixture of the first fluid and the second fluid, and wherein at least some of the one or more third fluid delivery parameters are different than the one or more first and second fluid delivery parameters, and means for outputting the one or more third fluid delivery parameters for controlling the medical pump to deliver the third fluid to a patient.

In another example, the disclosure is directed to a computer-readable storage medium containing instructions. The instructions cause a programmable processor to obtain one or more first fluid delivery parameters that at least partially define delivery of a first fluid within a downstream portion of a fluid path of a fluid delivery system, wherein a medical pump and a catheter of the fluid delivery system define at least a portion of the fluid path, obtain one or more second fluid delivery parameters that at least partially define delivery of a second fluid within an upstream portion of the fluid path upstream from the first fluid, wherein the second fluid comprises a therapeutic agent, determine, based on the one or more first fluid delivery parameters and the one or more second fluid delivery parameters, one or more third fluid delivery parameters that at least partially define delivery of a third fluid located between the first fluid and the second fluid in the fluid path, wherein the third fluid comprises a mixture of the first fluid and a third fluid, and wherein the one or more third fluid delivery parameters are different than the one or more, and output the one or more third fluid delivery parameters for controlling the medical pump to deliver the third fluid to a patient.

The details of one or more examples of the invention are set forth in the accompanying drawings and the description below. Other features, objects, and advantages of the invention will be apparent from the description and drawings, and from the claims.

DETAILED DESCRIPTION

Figure 1:
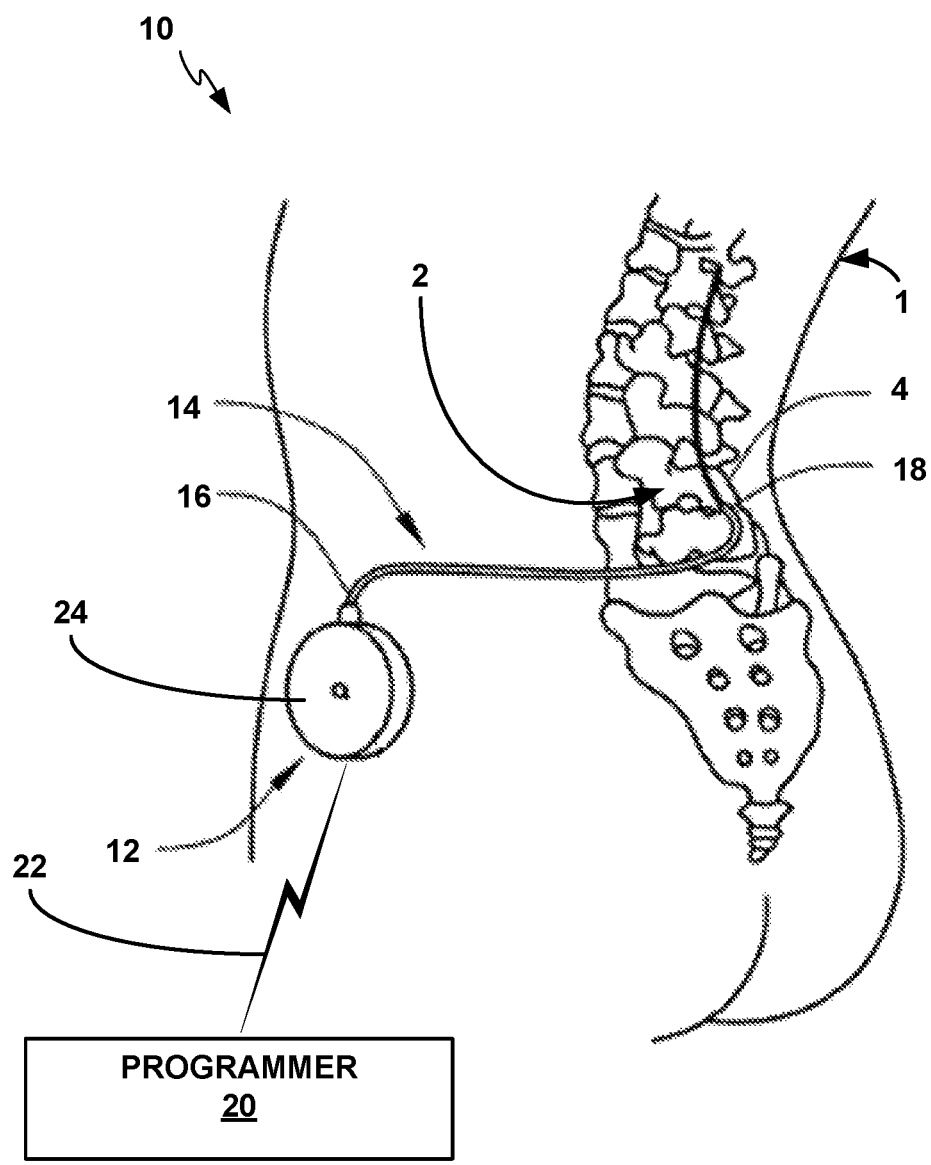
FIG. 1 is a conceptual diagram illustrating an example of a fluid delivery system, which includes an implantable medical device (IMD), e.g., a fluid delivery device including a medical pump, and an external programmer.

In general, the disclosure relates to systems and methods for scheduling, or controlling, drug delivery therapy. This scheduling may include transitioning between different deliveries of drugs (or other therapeutic fluids). The transition may include changing between different drug delivery sources (e.g., external and implanted drug pumps), changing between different concentrations of a drug, changing the type of one or more drugs being delivered to a patient, beginning initial drug delivery or ending drug delivery (e.g., weaning the drug concentration to reduce withdrawal symptoms). Timing of the delivery of a new drug and/or termination of the previous drug may affect the overall dose the patient receives.

Transition times used to change between different deliveries of a drug or different drugs may be calculated from a location in which a new drug is added to a fluid path. In other words, the time for moving drug from the reservoir to the patient was based on the dead space volume (e.g. the dead space of a catheter and pump) and the flow rate applied. The dead space volume, however, may include another fluid (e.g., saline, a drug of a different concentration than that of the drug in the reservoir, or any other therapeutic fluid). Therefore, the drug may diffuse or otherwise mix forward into the adjacent fluid in the catheter, and the fluid may mix backward to dilute the drug upstream in the catheter. Fluid may also mix upstream of the catheter, such as within one or more channels or passages of the pump.

As described herein, systems and techniques may be employed to provide a total dosing of a drug, during drug delivery transitions, that attempts to minimize overdosing and/or underdosing that occurs when switching abruptly between two different fluids. For example, the system may determine a flow rate and period of time during which to deliver at least a portion of the mixture of the two fluids to be delivered to the patient. The system may calculate a flow rate between the scheduled flow rate of a first fluid to be delivered and the scheduled flow rate of a second fluid to be delivered. Therefore, delivering the mixture of the fluids at the calculated flow rate may achieve a total dosage similar to the target prescribed dose.

The system may also be configured to determine the period of time, or volume of the mixed fluid, to deliver the mixed fluid to the patient at the calculated flow rate. A concentration profile may represent the extent to which two adjacent fluids mix with each other within the fluid path of the drug delivery system. In other words, the concentration profile may account for drug diffusion or mixing in fluid prior to a therapeutic agent reaching the patient. The system may calculate a longer period of time, or a greater volume, for fluids that exhibit greater mixing. Conversely, the system may calculate a shorter period of time, or a lower volume, for fluids exhibiting lesser mixing. The concentration profile may be determined experimentally, calculated by modeling the mixing of fluid within system, based on factors or characteristics of one or more fluids such as viscosity, diffusion rates, temperature, or any combination thereof. One or more sensors may detect values of any of these factors or characteristics for use in generating and/or updating in real-time the concentration profile and/or the applied flow rate of fluid.

After the delivery parameters (e.g., the flow rate, period of time, and/or volume) of the mixed fluid are determined by the system, the system may control delivery of all of the fluid using these delivery parameters. For example, the system may control delivery of a first fluid using a drug delivery schedule prescribed by a clinician and track the progress of the delivery by time and/or volume of fluid. In response to determining that the mixed fluid is being released at the outlet of the catheter, the system may switch the flow rate to the calculated flow rate of the mixed fluid. In response to determining that the mixed fluid (e.g., a fluid including a mixture of the first fluid and a second fluid) has been delivered, the system may again switch the flow rate, and other delivery parameters, to the drug delivery schedule prescribed for the second fluid. Therefore, the system may automatically transition between different drug delivery schedules when transitioning between two different drug types, two different drug sources with the same or different drugs, or two different concentrations of the same drug.

In other examples, the system may facilitate the generation of flexible drug delivery schedules. A drug delivery schedule may be generated using interchangeable "steps" that define respective delivery parameters that are assigned to one or more different "patterns" that define the time in which each step will define drug delivery. The system may receive user input selecting one or more patterns that each defines a recurring time period for delivering a drug. Within each pattern, the system may receive user input selecting one or more steps that each defines a respective set of drug delivery parameters for the respective step. Each of the one or more patterns may be associated with any stored step, such that a step can be assigned to any pattern desired by a user, such as a clinician.

As described herein, the flexible drug delivery schedules may be used before, after, and during the transition from one fluid (or drug) to the second fluid (or drug). For example, once a new, or second fluid is loaded into a reservoir of a fluid delivery device, the fluid delivery device may continue to use the previous flexible drug delivery schedule for the first fluid that remains within the fluid delivery device and/or catheter. The fluid delivery device may then continue to use flexible drug delivery schedules for the amount of mixed fluid (portion of fluid that includes a combination of the first and second fluids) and the second fluid, as desired. In other words, the fluid delivery device can apply respective flexible drug delivery schedules for any of the first fluid, mixed fluid, or second fluid because the fluid delivery device can model the amount of mixed fluid at the interface between the first and second fluid. In this manner, the fluid delivery device can provide more accurate dosing throughout the transition to and/or from different drugs. This process would be in contrast to some typical devices in which a single flow rate is used, instead of a previously used flexible drug delivery schedule, for the first fluid remaining in a catheter upon a second fluid being added to the reservoir of the fluid delivery device.

FIG. 1 is a conceptual diagram illustrating an example of a system 10, which includes implantable medical device (IMD) 12, e.g., a fluid delivery device including a medical pump, and external programmer 20. As shown in FIG. 1, IMD 12 may be configured to deliver a therapeutic agent, such as a pharmaceutical agent, for example a drug, insulin, pain relieving agent, anti-inflammatory agent, gene therapy agent, or the like, to a target site 2 within a patient 1. The therapeutic agent (e.g., a drug) is delivered via a catheter 14 that is coupled to IMD 12. Catheter 14 may comprise a plurality of catheter segments, or catheter 14 may be a unitary catheter. In the example shown in FIG. 1, target site 2 is proximate to spinal cord 4 of patient 1. System 10 may be referred to as a fluid delivery system, which may include a drug delivery system when the fluid contains one or more drugs or therapeutic agents.

A proximal end 16 of catheter 14 is coupled to IMD 12 while a distal end 18 of catheter 14 is positioned proximate target site 2. System 10 may also include an external programmer 20 that communicates with IMD 12 as needed, such as to provide or retrieve therapy information or therapy parameters associated with therapy delivery. For example, external programmer 20 may be configured to turn IMD 12 on or off, to deliver the initial therapy parameters for patient 1, to modify the therapy parameters, and so forth. In one example, external programmer 20 communicates with IMD 12 wirelessly 22, as shown in FIG. 1.

Although patient 1 is generally referred to as a human patient in the present disclosure, system 10 can be used with other mammalian or non-mammalian patients. IMD 12 may be employed to treat, manage or otherwise control various conditions or disorders of patient 1, including, e.g., pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, cardiovascular disease (e.g., arterial hypertension), or other disorders.

IMD 12 may be configured to deliver one or more therapeutic agents, alone or in combination with other therapies, including, e.g., electrical stimulation. For example, in some cases, IMD 12 may house a medical pump that delivers one or more pain-relieving drugs to patients with chronic pain, insulin to a patient with diabetes, or other fluids to patients with different disorders. IMD 12 may be implanted in patient 1 for chronic or temporary therapy delivery.

IMD 12 includes an outer housing 24 that is constructed of a biocompatible material that resists corrosion and degradation from bodily fluids, such as titanium or biologically inert polymers. IMD 12 may be implanted within a subcutaneous pocket within patient 1, such as at a location close to target site 2 or remote from target site 2 and reached by an extended catheter. For example, as shown in FIG. 1, IMD 12 may be implanted within the abdomen of patient 1 close to the position along spinal cord 4 where target site 2 is located. In other examples, IMD 12 may be implanted within other suitable sites within patient 1, which may depend, for example, on where target site 2 is located within patient 1, and the ease of implanting IMD 12 within suitable locations near target site 2. Examples implantation sites for IMD 12 may include the lower abdomen, back, upper chest, buttocks, and any other location that may depend upon the type of therapy, target site 2, the patient condition, etc.

Catheter 14 may be coupled to IMD 12 either directly or with the aid of a catheter extension (not shown). In the example shown in FIG. 1, catheter 14 traverses from the implant site of IMD 12 to target site 2 proximate to spinal cord 4. Catheter 14 is positioned such that one or more fluid delivery outlets of catheter 14 are proximate to one or more locations within patient 1. In the example shown in FIG. 1, IMD 12 delivers a therapeutic agent to one or more locations at target site 2 within patient 1. IMD 12 delivers a therapeutic agent to target site 2 proximate spinal cord 4 with the aid of catheter 14. For example, IMD 12 may be configured for intrathecal drug delivery into the intrathecal space or epidural space surrounding spinal cord 4.

In some examples, multiple catheters may be coupled to IMD 12 to target the same or different tissue or nerve sites within patient 1. Thus, although a single catheter 14 is shown connected to IMD 12 in FIG. 1, in other examples, system 10 may include multiple catheters or catheter 14 may define multiple lumens for delivering different therapeutic agents to patient 1 or for delivering a therapeutic agent to different tissue sites within patient 1. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed herein with reference to the example of FIG. 1.

IMD 12 may deliver one or more therapeutic agents to patient 1 according to one or more therapy programs. These therapy programs may be included in a drug delivery schedule. Example therapeutic agents that IMD 12 may be configured to deliver include insulin, morphine, hydromorphone, bupivacaine, clonidine, other analgesics, genetic agents, antibiotics, nutritional fluids, analgesics, hormones or hormonal drugs, gene therapy drugs, anticoagulants, cardiovascular medications or chemotherapeutics. A therapy program, generally speaking, may set forth different therapy parameters, such as a therapy schedule specifying programmed doses, dose rates for the programmed doses, and specific times to deliver the programmed doses.

The therapy programs may be a part of a program group for therapy, wherein the group includes a plurality of constituent therapy programs and/or drug delivery schedules. In some examples, IMD 12 may be configured to deliver a therapeutic agent to patient 1 according to one or more different therapy programs of a drug delivery schedule on a selective basis. IMD 12 may include a memory to store the drug delivery schedule, one or more therapy programs, instructions defining the extent to which patient 1 may adjust therapy parameters, switch between therapy programs, or undertake other therapy adjustments. Patient 1 may select and/or generate additional therapy programs for use by IMD 12 via external programmer 20 at any time during therapy or as designated by the clinician.

In one example, programmer 20 is an external computing device that is configured to communicate with IMD 12, such as via a wireless communications link 22. For example, programmer 20 may be a clinician programmer that the clinician uses to communicate with IMD 12, such as retrieving data and providing instructions regarding delivery of drugs to patient 1. Alternatively, programmer 20 may be a patient programmer that allows patient 1 to view and modify therapy parameters. A clinician programmer may include additional or alternative programming features, relative to a patient programmer, which may have more limited features such as limited programming capability. For example, more complex or sensitive tasks may only be allowed by the clinician programmer to prevent patient 1 from making undesired changes to the operation of IMD 12.

Programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include one or more of a keypad, buttons, a peripheral pointing device, touch screen, voice recognition, or another input mechanism that allows the user to navigate through the user interface of programmer 20 and provide input such as selecting one or more delivery parameters for generating a drug delivery schedule.

In other examples, rather than being a handheld computing device or a dedicated computing device, programmer 20 may be a larger workstation or a separate application within another multi-function device. For example, the multi-function device may be a cellular phone, smartphone, tablet computing device, personal computer, laptop or notebook computer, workstation computer, or personal digital assistant that can be configured to an application to simulate programmer 20. Alternatively, a notebook computer, tablet computer, or other personal computer may execute an application to function as programmer 20, e.g., with a wireless adapter connected to the personal computer for communicating with IMD 12.

When programmer 20 is configured for use by the clinician, programmer 20 may be used to transmit initial programming information to IMD 12. This initial information may include hardware information for system 10 such as the type of catheter 14, the position of catheter 14 within patient 1, the type of therapeutic agent(s) delivered by IMD 12, a baseline orientation of at least a portion of IMD 12 relative to a reference point, therapy parameters of therapy programs (e.g., a drug delivery schedule) stored within IMD 12 or within programmer 20, and any other information the clinician desires to program into IMD 12.

A clinician uses programmer 20 to program IMD 12 with one or more therapy programs that define the therapy delivered by IMD 12. During a programming session, the clinician may determine one or more therapy programs, which may include one or more drug delivery schedules, programmed doses, dose rates of the programmed doses, and specific times to deliver the programmed doses that may provide effective therapy to patient 1. Patient 1 may provide feedback to the clinician as to the efficacy of a specific therapy program being evaluated or desired modifications to the therapy program. Once the clinician has identified one or more programs that may be beneficial to patient 1, patient 1 may continue the evaluation process and determine which dosing program or therapy schedule best alleviates the condition of patient 1 or otherwise provides efficacious therapy to patient 1.

In some cases, programmer 20 may be configured for use by patient 1 (e.g., as a patient programmer). When configured as a patient programmer, programmer 20 may have limited functionality in order to prevent patient 1 from altering critical functions or applications that may be detrimental to patient 1. In this manner, programmer 20 may only allow patient 1 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 1 when therapy is being delivered or when IMD 12 needs to be refilled or when the power source within programmer 20 or IMD 12 needs to be replaced or recharged. The reservoir of IMD 12 may be refilled with the same drug with same concentration, the same drug with a different concentration, or a different drug. IMB 12 may provide a bridge bolus when transitioning between difference concentrations or different drugs, as described herein. IMB 12 may provide a prime bolus when initially delivering an inert fluid (e.g., water or saline) located within catheter 14 prior to delivering drug contained within the reservoir of IMB 12. Alternatively, IMB 12 may provide the inert fluid at the end of drug delivery to wean the patient off of a drug previously delivered. In other examples, programmer 20 may be configured as a home monitoring device or other data transfer device that receives instructions from a remote clinic via a network and then transmits the received instructions to IMB 12 during the next connection session.

Whether programmer 20 is configured for clinician or patient use, programmer 20 may communicate to IMD 12 or any other computing device via wireless communication. Programmer 20, for example, may communicate via wireless communication link 22 with IMB 12 using any of a number of radio frequency (RF) telemetry techniques. Programmer 20 may also communicate with another programmer or computing device via a wired or wireless connection using any of a variety of local wireless communication techniques, such as proximal electromagnetic induction (e.g., H-field communication), RF communication according to one or more specification sets, such as the Medical Implant Communication Service (MICS) specification set, Medical Implant Telemetry System (MITS), Medical Data Service (MEDS), 802.11, or Bluetooth specification sets, infrared (IR) communication according to the IRDA specification set, or other standard or proprietary telemetry protocols. Programmer 20 may also communicate with another programmer or computing device via exchange of removable media, such as magnetic or optical disks, or memory cards or sticks. Further, programmer 20 may communicate with IMD 12 and another programmer via remote telemetry techniques, communicating via a local area network (LAN), wide area network (WAN), public switched telephone network (PSTN), satellite link, or cellular telephone network, for example. In other examples, multiple different communication techniques may be used to transmit data for security and/or redundancy purposes.

As described herein, system 10 may utilize delivery parameters of known fluids and/or a concentration profile of one or more fluids to determine one or more delivery parameters of a fluid mixture located between two known fluids within system 10. For example, system 10 may determine a flow rate for delivering the mixture of two fluids in order to transition therapy from the first fluid to a second fluid located upstream from the first fluid. System 10 may also determine a period of time for delivering the mixture of fluid at the determined flow rate. In this manner, system 10 may determine one or more delivery parameters to control the transition between two fluids that may minimize both overdosing and underdosing during the transition between drug delivery sources and/or concentrations of the drug in the fluids.

One or more of IMD 12 and programmer 20 may include one or more processors configured to perform various functions related to determining delivery parameters and/or controlling delivery according to the determined delivery parameters. In one example, one or more of IMD 12 and programmer 20 may be configured to facilitate the transition in drug delivery to patient 1. System 10 may obtain one or more first fluid delivery parameters that at least partially define delivery of a first fluid within a downstream portion of a fluid path of drug delivery system 10. A medical pump housed within IMD 12 and catheter 14 may define at least a portion of the fluid path. System 10 may also obtain one or more second fluid delivery parameters that at least partially define delivery of a second fluid within an upstream portion of the fluid path upstream from the first fluid. Like the first fluid, the second fluid may include a therapeutic agent. However, the second fluid may be from a different source than the first fluid, be the same type of fluid with a different concentration of drug than the first fluid, or be a different type of fluid than the first fluid. The second fluid may also be located within a reservoir of IMD 12. In this manner, the second fluid may be intended to replace the first fluid for delivery to patient 1.

System 10 may also determine, based on the one or more first fluid delivery parameters and the one or more second fluid delivery parameters, one or more third fluid delivery parameters that at least partially define delivery of a third fluid located between the first fluid and the second fluid in the fluid path. At the interface between the first and second fluids, some mixing of the first and second fluids may occur. Since this mixed fluid may not have the same therapeutic properties as either the original first and second fluids, patient 1 may benefit from delivery of the mixed fluid (i.e., the third fluid) at different parameter values than either the first or second fluids. Therefore, determination of the one or more third fluid delivery parameters may effectively define the transition between old and new fluids (e.g., the first and second fluids). System 10 may then be configured to output the one or more third fluid delivery parameters for controlling IMD 12 to deliver the third fluid to patient 1.

System 10 may also determine one or more of the delivery parameters that at least partially define the delivery of at least a portion of the mixed fluid during the transition between the first and second fluids. For example, system 10 may calculate a volume of the mixed fluid, a duration of delivery of the mixed fluid, and a flow rate for delivering the mixed fluid. These delivery parameters may be calculated from one or more constraints provided by a user, such as user input defining the duration for delivering the mixed fluid (i.e., the time period for transitioning between the first and second fluid. Alternatively, user input may provide a desired flow rate or a flow rate factor that specifies how similar the flow rate for the mixed fluid should be with respect to the prescribed flow rate of either the first fluid or the second fluid. For example, the flow rate factor may request a relatively higher flow rate to guard against underdosing or a relatively lower flow rate to guard against overdosing during the transition between the first and second fluids.

In order to determine the delivery parameters of the mixed fluid, system 10 may obtain one or more fluid delivery parameters of the first and second fluids. For example, system 10 may obtain at least one of a concentration of the first fluid, a flow rate of the first fluid, and a volume of the first fluid and obtain at least one of a concentration of the second fluid, a flow rate of the second fluid, and a volume of the second fluid. The fluid parameters of the first and second fluid may provide constraints for the mixed fluid. For example, the flow rates of the first and second fluids, which may be predetermined flow rates to achieve prescribed dosages of a therapeutic agent within the first and second fluids, may provide upper and lower bounds to the flow rate of the mixed fluid. In other words, system 10 may select a flow rate for the mixed fluid that is between the first and second fluid flow rates because the concentration of the therapeutic agent of the mixed fluid may generally be between the concentrations of the first and second fluids. In addition, system 10 may obtain the volume of the first fluid to estimate the volume of the mixed fluid. System 10 may calculate the volume of the first fluid from the known volume of catheter 14 and any passages or channels within IMD 12 downstream from the reservoir of IMD 12.

In one example, system 10 may obtain the volume of the first fluid and the flow rate of the first fluid. The volume of the first fluid may be calculated from the known volume of the fluid path out of IMD 12 and catheter 14 and a concentration profile of the first and second fluid, as described below. The flow rate for the first fluid may be obtained from a drug delivery schedule for the first fluid or some other predetermined flow rate. System 10 may then calculate, based on the volume and the flow rate of the first fluid, the period of time required to deliver the first fluid to the patient at the obtained flow rate. System 10 may also determine, based on the first fluid and the second fluid, the volume of the mixed fluid between the first fluid and the second fluid sourced from a reservoir of IMD 12. The volume of the mixed fluid may be determined (e.g., calculated or estimated) based on one or more dimensions of the fluid path and/or a concentration profile that characterizes the mixing, or diffusion, of a therapeutic agent between the first and second fluids. Based on the delivery parameters of the first and second fluids, system 10 may then determine the flow rate for delivering the mixed fluid to patient 1. In addition, system 10 may determine the period of time for delivering the mixed fluid out of catheter 14. This period of time may be calculated from the estimated volume of the mixed fluid and the flow rate for the mixed fluid.

The volume of the mixed fluid, and the volume of the corresponding first fluid, may be determined based on a concentration profile for the first fluid, the second fluid, or the interface between the first fluid and the second fluid. The concentration profile may represent an estimation of the change in concentration of a therapeutic agent throughout the mixture. In other words, the concentration profile of the therapeutic agent or drug may represent the differential drug concentration of the entire fluid volume within catheter 14 and possibly other passages or channels of IMD 12 downstream of the reservoir. When two fluids come in contact with each other, the boundary between the fluids may not remain highly defined. Instead, respective portions of the two fluids mix with each other or undergo some diffusion at the boundary. The result is a gradient, or profile, that represents the interface between the two fluids. In other words, there is some volume of fluid at the interface that contains a portion of both fluids. This volume of fluid at the interface may be described as the mixed fluid. The concentration profile of the drug within this interface may thus be an estimate the concentration of a drug at various positions within the fluid contained within the fluid path of IMD 12 and catheter 14 (e.g., within catheter 14 and/or one or more passages or channels within IMD 12.

In some examples, the concentration profile may be an equation that represents the magnitude of diffusion (e.g., a diffusion coefficient) and gradient of such diffusion. The concentration profile may be specific to the first fluid and/or the second fluid, the therapeutic agent within the fluid, diffusion rates of a therapeutic agent in one or more fluids, the length and/or diameter of the fluid path, the pressure of fluid within the fluid path, the temperature of the fluids, viscosity of one or more of the fluids (e.g., viscosity of the fluid and/or therapeutic agents within the fluid), or any other aspect or mixing characteristics that may affect the mixing of the first and second fluids. One or more sensors may be used to determine values for one or more of these factors that affect the concentration profile. For example, one or more sensors may sense viscosity, flow rates, or any other fluid mixing characteristics. The sensor data may be provided in real-time to establish real-time concentration profiles in response to receiving the sensor data. In this manner, the concentration profile may provide information effectively modeling the concentration of a therapeutic fluid throughout the fluid path. In other examples, the concentration profile may include a simple estimate of the mixing between the two fluids. In this manner, the concentration profile may be a multiplication factor that can be applied to the length of the fluid path (e.g., catheter 14) to calculate an estimated length of the catheter that may include the mixed fluid. The volume of the mixed fluid may then be calculated from this estimated length of catheter 14 that includes the mixed fluid. In some examples where fluid mixes within IMD 12, the volume of fixed fluid may be calculated from the estimated volume of channels within IMD 12 upstream from catheter 14, in addition to the length of catheter 14. The concentration profile may also indicate the gradient of the concentration within the mixed fluid, such as a liner gradient, polynomial gradient, exponential gradient, or any other mathematical representation of how the concentration of therapeutic agent changes over the length of the fluid path between the full concentrations of each of the first and second fluids. In some examples, a concentration profile may be experimentally determined for one or more given factors and extrapolated to fit different situations. Alternatively, system 10 or another device may automatically calculate the concentration profile based on one or more of the factors above.

In this manner, system 10 may use the concentration profile to estimate one or more delivery parameters of the mixed fluid. After obtaining the concentration profile, system 10 may determine the volume of the first fluid and the mixed fluid that will exit catheter 14. The volumes may be determined based on the concentration profile and at least one dimension (e.g., length and/or diameter). In other words, the concentration profile may indicate how the first and second fluids mix within the fluid path. Therefore, the actual volume of the full concentration of just the first fluid may decrease due to some mixing with the second fluid. Each of the volumes of the first fluid and the mixed fluid may be used to calculate the period of time during which IMD 12 should deliver each of the first fluid and the mixed fluid.

System 10 may also determine the flow rate with which to deliver the mixed fluid from IMD 12 and catheter 14 to patient 1. System 10 may adjust the flow rate for the mixed fluid to accommodate the difference in concentration of the therapeutic agent between the first and second fluids. In other words, the mixed fluid may be delivered at one or more flow rates in order to maintain a total output dosage of the therapeutic agent to minimize overdosing and/or underdosing during delivery of the mixed fluid when transitioning between the first and second fluids. For example, system 10 may select the mixed fluid flow rate value between the flow rates of the first and second fluids. The first and second fluids may be delivered at different flow rates (e.g., incremental or continuously changing flow rates) to achieve a similar dosage even though the fluids have different concentrations of a therapeutic fluid. Since the mixed fluid may have a concentration of the therapeutic fluid between the concentrations of the first and second fluid, system 10 may select the flow rate for the mixed fluid to also be between the flow rates of the first and second fluid. Delivering the mixed fluid at this flow rate may achieve a dosage of the therapeutic fluid similar to that of the first and second fluid delivered at the prescribed flow rate. For example, if the first fluid is delivered at a flow rate of approximately 0.2 milliliters (mL) per hour and the second fluid is delivered at a flow rate of approximately 0.4 mL per hour, system 10 may deliver the mixed fluid at a flow rate of approximately 0.3 mL per hour.

In some examples, system 10 may determine a plurality of different flow rates with which to deliver the mixed fluid to patient 1. The multiple flow rates for delivering the mixed fluid may be selected to maintain the delivered dosage of the therapeutic agent within the mixture based on the changing concentration of the therapeutic agent within the mixed fluid exiting catheter 14. In this manner, system 10 may select a plurality of different flow rates to match, or approximate, different portions of the concentration profile of the mixed fluid. In other words, each of the plurality of matching flow rates may be selected according to respective different portions of the concentration profile to achieve a more uniform dosage of drug than would be possible from a single flow rate for the entire concentration profile of the mixed fluid. For example, if the first fluid has a concentration of approximately 4.0 milligrams per mL (mg/mL) and the second fluid has a concentration of approximately 8.0 mg/mL (e.g., system 10 is transitioning to a higher concentration), the concentration of the therapeutic agent may vary between 4.0 mg/mL and 8.0 mg/mL within the mixed fluid. Therefore, system 10 may iteratively decrease the flow rate when delivering the mixed fluid to accommodate the changes in concentration. If system 10 transitions from a higher concentration to a lower concentration, system 10 may select iteratively increasing flow rates. In some examples, the flow rates may increase at a linear rate. In other examples, the flow rates may change according to a polynomial curve or other non-linear rate that may more closely match the concentration profile of the therapeutic agent within the mixed fluid.

System 10 may use the determined flow rates, volume, and/or period of time for delivering the mixed fluid to control the transition in drug delivery between the first fluid and the second fluid. For example, a processor of IMD 12 may control the medical pump (not shown in FIG. 1) of IMD 12 to deliver the first fluid at a respective flow rate and period of time. IMD 12 may control the delivery of the first fluid according to the drug delivery schedule until the determined volume of the first fluid has been delivered and the mixed fluid has reached the exit of catheter 14. Responsive to the period of time for delivering the first fluid elapsing, IMD 12 may control the medical pump to deliver the mixed fluid at the second flow rate for the second period of time. Responsive to the period of time for delivering the mixed fluid elapsing, IMD 12 may control the medical pump to deliver the second fluid at a third flow rate, wherein each of the first flow rate, the second flow rate, and the third flow rate of the respective fluids are different flow rates. In other words, IMD 12 may control the medical pump to adjust the flow rate of fluid at multiple times during the transition from the first fluid to the second fluid.

In some examples, IMD 12 may directly control the medical pump to deliver fluid based on stored instructions, such as the drug delivery schedule and determine delivery parameters for the mixed fluid. In other examples, programmer 20 may transmit commands to IMD 12 for controlling the medical pump. In this manner, a single device of system 10 may control the adjustments to the medical pump or multiple devices of system 10 may collectively control the medical pump and delivery of fluid to patient 1.

As described herein, system 10 may track the time and/or volume of each fluid delivered to patient 1. For example, system 10 may deliver the first fluid according to the prescribed drug delivery schedule until system 10 determines that the volume of the first fluid has been delivered and the mixed fluid has arrived at the exit of catheter 14. In other words, system 10 may calculate, based on the volume of the first fluid and the one or more sets of the delivery period and the flow rate from the drug delivery schedule, a period of time for delivering the first fluid to the patient. In other words, system 10 (e.g., IMD 12 and/or programmer 20) may monitor the volume of fluid being delivered via tracked pump strokes and stroke volume and/or one or more fluid flow sensors that monitor the volume of flowing through one or more locations of the fluid path downstream from the medical pump. System 10 may then switch from the drug delivery schedule and deliver the mixed fluid at the determined flow rate for the determined period of time. However, system 10 may also track the volume of the mixed fluid and continue drug delivery according to the drug delivery schedule of the first fluid with the modified flow rate determined for the mixed fluid. System 10 may then, in response to determining that the mixed fluid has been delivered from catheter 14, control delivery of the second fluid according to the drug delivery schedule for the second fluid.

By tracking time of fluid delivery at a certain flow rate or volume of a fluid delivered to patient 1, system 10 may adjust when to switch between different drug delivery schedules during the transition from a first fluid to a second fluid based on unscheduled changes to therapy. For example, patient 1 may interact with a patient programmer (e.g., programmer 20) to pause or stop delivery of fluid, change the flow rate of the fluid, or change any other parameter that affects the delivery of the fluid. IMD 12, for example, may track the time and/or volume of fluid to mark where the drug delivery schedule was interrupted and track the volume of fluid delivered during the unscheduled change to therapy. Then, once the unscheduled change in therapy reverts back to therapy defined by the drug delivery schedule, system 10 may know how much volume of fluid (and the dose of drug) was delivered to patient 1 and adjust the remaining drug delivery schedule, adjust the transition time when transitioning between two different fluids, or otherwise compensate drug delivery based on the unscheduled change in fluid delivery.

In other examples, system 10 may implement a lockout feature that prevents patient-initiated changes to therapy during a transition between two different fluids (e.g., during a prime bolus, during a bridge bolus, or at any time between prescribed drug delivery schedules). These patient-initiated changes to therapy may be requests for additional drug and/or requests to pause or stop fluid delivery. In this manner, the lockout feature may prevent a patient from altering the total output dosage of one or more drugs during the transition. In some examples, the lockout feature or adjustments to therapy available to a user (e.g., a patient or clinician) may be dependent upon which fluid is currently exiting the catheter. System 10 may determine which fluid (e.g., the first fluid, the second fluid, or the third mixed fluid) is currently exiting the catheter to the patient and allow adjustments based on which fluid is being delivered. For example, system 10 may disable any adjustments to delivery of the third (mixed) fluid, limit fluid flow increases or dosing to a first level for the first fluid, and limit fluid flow increases or dosing to a second level for the second fluid. Programmer 20 may change available inputs in a user interface for different fluids as well. These available adjustments may also be specific to different drug delivery schedules currently used to deliver the current fluid, but these different drug delivery schedules may also be selected based on which fluid is being delivered out of the catheter.

The transition between fluids delivered from catheter 14 may occur for a variety of drug delivery transitions, such as delivering a prime bolus or a bridge bolus. In the example of a newly implanted IMD 12 and catheter 14, the reservoir of IMD 12, IMD 12 may deliver a prime bolus. Catheter 14 may be filled with the first fluid that may be an inert fluid that does not include a therapeutic agent or does not otherwise provide therapy to patient 1. The inert fluid may include water, saline, or any other fluid that is not delivered to provide therapy. At the boundary between the catheter fluid and the drug in the reservoir of IMD 12, some drug mixes with the priming fluid. System 10 may thus deliver a prime bolus to prime the system, where the prime bolus may include the inert first fluid and a mixture of the inert fluid and the second fluid including a therapeutic agent. System 10 may implement different flow rates to quickly deliver the inert fluid and then slow down the flow rate as the mixed fluid is delivered before reaching an even slower flow rate for the second fluid. Conversely, IMD 12 may be filled with an inert fluid after delivery of a drug to wean patient 1 off of the drug previously delivered.

In the example of refilling an implanted IMD 12 with a drug of a different concentration than the previous concentration delivered to patient 1, drug with the previous concentration may still be within catheter 14 whereas the new concentration of the drug is contained within the reservoir. This transition may be referred to as delivering a bridge bolus. The interface between the fluids of each concentration may contain mixing of the concentrations such that the concentration of drug at the interface is of some gradient between the two concentrations. The concentration profile of the drug may represent the mixing of drug at this interface to estimate the actual concentration for a given volume of the fluid at the interface.

System 10 may also include one or more display devices. For example, programmer 20 or another device may include a display device configured to present various information related to the drug delivery schedule, fluid being delivered, drug concentrations, flow rate, target prescribed dose, and/or any other aspect of therapy. In one example, one or more of IMD 12, programmer 20 and/or external drug pump 26 may be configured to output, for presentation at the display device, a graph of the flow rate changes over time, a graph of the total output dose over time, and/or a graph of the output concentration over time. In this manner, system 10 may provide feedback to the user regarding the progress of therapy and the transition between fluids within IMD 12 and catheter 14.

In addition to controlling the transition between two different fluids, system 10 may generate drug delivery schedules using a variety of different "patterns" and "steps" that together define the delivery of fluid from IMD 12 over time. Instead of requiring the drug delivery schedule to be managed in a calendar-like framework, system 10 may facilitate flexible programming by allowing a user to populate a number of different patterns with a number of different steps defining therapy. In other words, each pattern may define a time period in which drug delivery occurs, and each step within the respective pattern may define the delivery parameters for controlling the delivery of fluid to patient 1, such as flow rate and duration of time for providing the flow rate. In this manner, each pattern may point to one or more different steps to populate the delivery schedule during the time of each pattern. After the user defines each pattern and the respective steps of each pattern, system 10 may generate the drug delivery schedule. These patterns and/or steps of the drug delivery schedule may be used to gradually increase dosage of a new therapeutic agent to patient 1 and/or gradually decrease dosage of an old therapeutic agent to patient 1.

Moreover, system 10 may provide one or more different features that accommodate faults during the delivery of therapy and attempt to maintain therapy for patient 1. For example, system 10 may store a copy of the drug delivery schedule in a non-volatile memory of IMD 12 and/or programmer 20. If the volatile memory of IMD 12 is corrupted, for example, an original copy of the drug delivery schedule may be retrieved. In another example, IMD 12 and/or programmer 20 may track the time and/or volume of fluid delivered during delivery by the drug delivery schedule and/or the transition between two different fluids. For example, if fluid flow is disrupted during a transition period, IMD 12 may retain the known delivered volume of each fluid so that the amount of fluid, and which fluid, within catheter 14 is known. When normal delivery of fluid is restarted, IMD 12 may resume delivery of fluid using the known volume of fluid that remains to be delivered from catheter 14. In addition, IMD 12 and/or programmer 20 may provide alerts or other instructions to a user identifying the amount of fluid delivered, the point in the transition between fluids, and any other information that may indicate the dosage that patient 1 has received prior to and/or during the fault condition.

Figure 2:
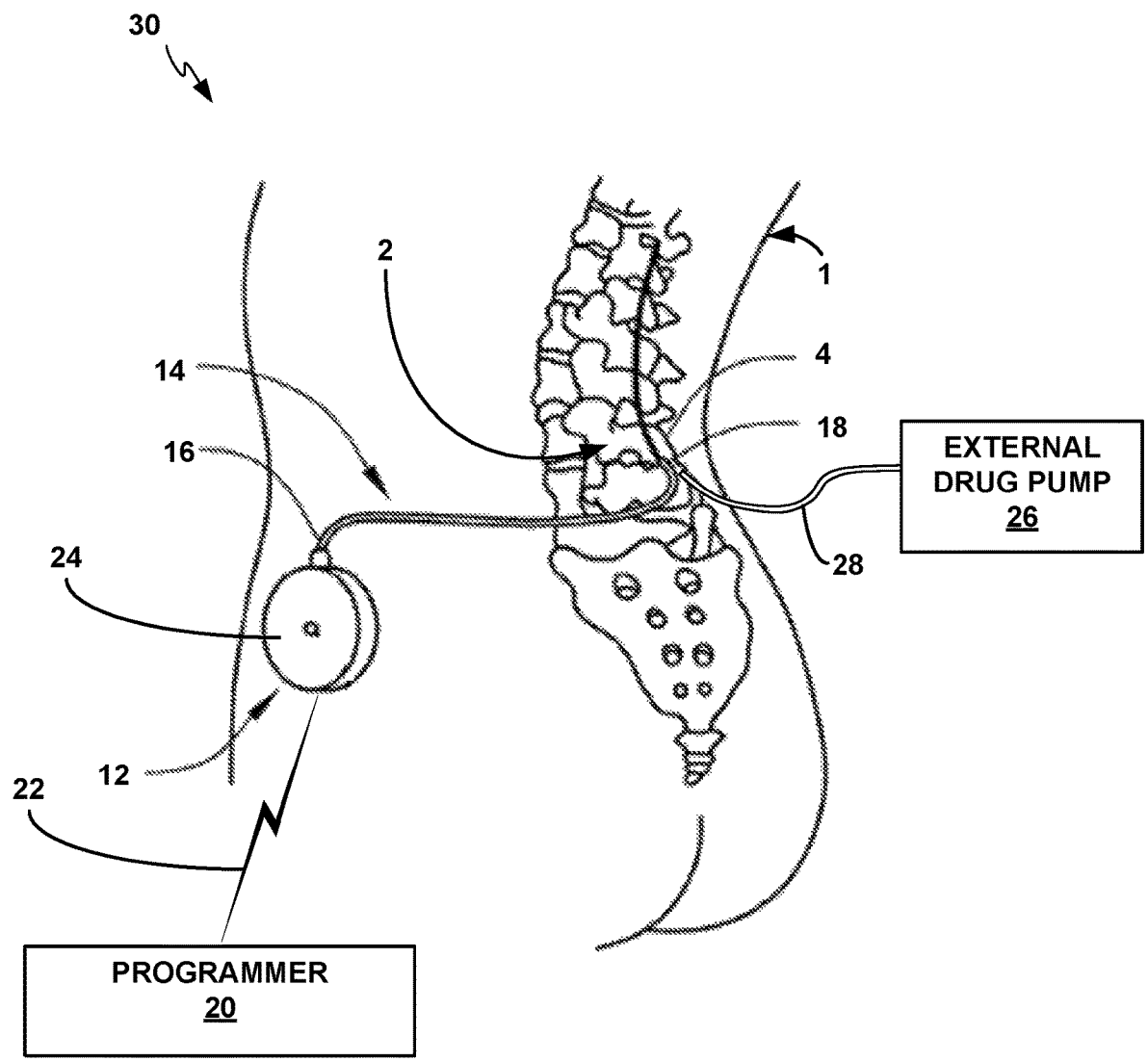
FIG. 2 is a conceptual diagram illustrating an example of a fluid delivery system, which includes an implantable medical device (IMD) for delivering a fluid to a patient, e.g., a fluid delivery device with a medical pump, and an external drug pump.

FIG. 1 is described with respect to transition of drug delivery from a single drug source (e.g., IMD 12). In other examples, transitions may occur between an external drug pump 26 and IMD 12, such as when external drug pump 26 is being removed after IMD 12 is implanted within patient 1 (as shown in the example of FIG. 2). In other examples, two or more external drug pumps may be used to delivery drug prior to the transition to IMD 12 or external drug pump 26 may be transitioned to a different external drug pump. In each of these transitions, a prime bolus may be delivered to patient 1 to initiate delivery with the new device prior to termination of drug delivered from the previous device. In other examples, the transition of drug delivery may be between two different concentrations of a drug or two different types of drugs that occurs when the reservoir of IMD 12 is refilled. This transition may referred to as a bridge bolus which includes the amount of previous fluid remaining within the catheter after the new drug or new concentration of drug is added to the reservoir.

System 10 may be configured to deliver any one or more different types of drugs. For example, system 10 may be used to deliver morphine, baclofen, ziconotide, various proteins, or any other therapeutic agent directed for treatment of a patient condition. These therapeutic agents are only examples, and system 10 may not be limited to any type of drug deliverable for treatment of patient 1. Furthermore, one or more components of system 10 may be selected to be compatible with any therapeutic agent of fluid to be delivered to patient 1. Each of the different fluids (e.g., the first fluid, the second fluid, and the third (mixed) fluid) may include one or more different types of therapeutic agents. In this manner, one or more fluids may have a "drug cocktail" or mixture of two or more therapeutic agents, which may be prescribed by a clinician.

Although the target therapy delivery site described with reference to the foregoing examples is proximate to the spinal cord of a patient, other applications of therapy systems in accordance with this disclosure include alternative delivery sites. In some examples, the target delivery site may be proximate to different types of tissues including, e.g., nerves, e.g. sacral, pudendal or perineal nerves, organs, muscles or muscle groups. In one example, a catheter may be positioned to deliver a therapeutic fluid to a deep brain site or within the heart or blood vessels (e.g., intravenous infusion). For example, system 10 may be configured to deliver a therapeutic fluid (e.g., Treprostinil) to the heart of patient 1 in order to treat symptoms related to pulmonary arterial hypertension (PAH). Since patient 1 may be sensitive to small dosage changes of Treprostinil, the concentration profile and target transition dose described herein may be used to minimize the risk of an overdose, and an underdose, of Treprostinil to patient 1 when a drug transition must occur during therapy.

Delivery of a therapeutic fluid within the brain may help manage a number of disorders or diseases including, e.g., chronic pain, diabetes, depression or other mood disorders, dementia, obsessive-compulsive disorder, migraines, obesity, and movement disorders, such as Parkinson's disease, spasticity, and epilepsy. Catheter 14 may also be positioned to deliver insulin to a patient with diabetes. In other examples, the system may deliver a therapeutic fluid to various sites within a patient to facilitate other therapies and to manage other conditions including peripheral neuropathy or post-operative pain mitigation, ilioinguinal nerve therapy, intercostal nerve therapy, gastric drug induced stimulation for the treatment of gastric motility disorders and/or obesity, and muscle stimulation, or for mitigation of peripheral and localized pain e.g., leg pain or back pain.

FIG. 2 is a conceptual diagram illustrating an example fluid delivery system 30, which includes IMD 12 for delivering a fluid to patient 1, e.g., a fluid delivery device with a medical pump, and external drug pump 26. System 30 of FIG. 2 may be substantially similar to system 10 of FIG. 1. However, system 30 also includes external drug pump 26. In this manner, patient 1 may receive drug delivery therapy from both of IMD 12 and external drug pump 26 at the same time. This simultaneous drug delivery from two sources may occur when transitioning from one source to the other source, such as when transitioning from external drug pump 26 to IMD 12.

In addition to IMD 12, external drug pump 26 may be used to deliver drug to patient 1 at or near target site 2 via catheter 28. Only one catheter 28 will be described herein, but other examples may include two or more catheters implanted within patient 1 and fluidically coupled to external drug pump 26. External drug pump 26 may include a drug reservoir, one or more processors, memory, and other components for controlling delivery of drug to patient 1. In some examples, programmer 20 may be configured to receive data from external drug pump 26 and/or transmit instructions for controlling external drug pump 26. External programmer 26 may also include a user interface (e.g., a display device and/or input device) to present information to a user and receive instructions from a user such as starting and stopping drug delivery. Although IMD 12 is described coupled to catheter 14 different than catheter 28 coupled to external drug pump 26, other examples of system 30 may include a single catheter coupled to both IMD 12 and external drug pump 26 (either at different times or via two proximal segments that each couple to the respective IMD 12 and external drug pump 26.

Patient 1 may receive drug from only external drug pump 26 or IMD 12. However, patient 1 may receive drug (e.g., the drug in fluid from respective sources) from both of external drug pump 26 and IMD 12 during one or more periods of time. For example, patient 1 may receive drug from external drug pump 26 on a temporary basis before IMD 12 can be implanted. Once IMD 12 is implanted within patient 1 and catheter 14 is positioned at target site 2, a clinician may transition drug delivery from external drug pump 26 to IMD 12 before external drug pump is turned off and catheter 28 is removed. In other words, IMD 12 may be controlled to deliver a prime bolus to patient 1 while external drug pump 26 continues to deliver drug to patient 1. During this transition period that may include the prime bolus, drug may be delivered to patient 1 simultaneously from external drug pump 26 and IMD 12 to minimize the time and amount by which patient 1 is underdosed and minimize the time and amount by which patient 1 is overdosed during this simultaneous delivery.

In some examples, the same catheter is used when transitioning between external drug pump 26 and IMD 12. For example, if the external drug pump 26 is first delivery fluid to patient 1 via catheter 28, catheter 28 is removed from external drug pump 26 and attached to IMD 12. In other examples, an extension portion of catheter 28 is removed prior to attaching the shorter remainder of catheter 28 to IMD 12. External drug pump 26 may also be used for temporary purposes instead of IMD 12, such as during surgery or when the catheter and IMD 12 cannot be implanted on the same day. In this manner, catheter 14 may be switched from IMD 12 to external drug pump 26, and back to IMD 12 again. A catheter extension may be used in some situations.

As described herein, system 30 may utilize different flow rates and a concentration profile of a drug within fluid to achieve a desired dosing of the drug during the transition. During the period in which drug is delivered from both of external drug pump 26 and IMD 12, system 30 may control IMD 12 and/or external drug pump 26 to deliver fluid at a reduced flow rate during the transition to minimize possible overdosing of the drug. For example, external drug pump 26 may continue to deliver drug at the prescribed flow rate during the initial delivery of fluid from IMD 12. IMD 12 may deliver a prime bolus (e.g., the inert fluid in catheter 14) at a fast flow rate to eject the inert fluid from catheter 14. In response to IMD 12 determining that the inert fluid, or the first fluid, has been expelled from catheter 14, IMD 12 may decrease the flow rate because drug in the mixed fluid may begin to reach patient 1. Once a predetermined volume of the mixed fluid (e.g., partial or complete delivery of the mixed fluid) is delivered from catheter 14, IMD 14 may further decrease the flow rate to the prescribed flow rate of the second fluid and transmit a command to programmer 20 to terminate delivery from external drug pump 26. In some examples, IMD 12 may select lower flow rates for the mixed fluid than would be selected if IMD 12 was the only source of drug due to the continued delivery of drug from external drug pump 26. In other examples, IMD 12 may select higher flow rates for the mixed fluid than would be selected if IMD 12 was the only source of drug when drug delivery from external drug pump 26 is terminated prior to delivery of the mixed fluid. Alternatively, external drug pump 26 may be turned off during delivery of the mixed fluid from IMD 12.

In other examples, system 30 may coordinate the flow rates used to deliver fluid from IMD 12 and external drug pump 26 at the same time. In other words, system 30 may ramp up flow rates from IMD 12 simultaneously with a ramp down of flow rates from external drug pump 26. Programmer 20 may control both of IMD 12 and external drug pump 26, or a user may manually control the flow rates of external drug pump 26 and/or IMD 12 according to instructions provided by programmer 20. For example, the decrease in flow rate from external drug pump 26 may correspond to an increase in flow rate from IMD 12 that accounts for the concentration profile of the drug within the mixed fluid of IMD 12 and catheter 14. In this manner, the combined drug delivered from IMD 12 and external drug pump 26 may provide a total dosage during delivery of the mixed fluid that is estimated to be similar to a prescribed dosage for patient 1. External drug pump 26 and IMD 12 may each implement one or more different flow rate values during the transition period. The delivery parameters (e.g., flow rates, fluid volumes, and delivery times) during the transition period described herein may be generated from a concentration profile and one or more prescribed total dosages. Programmer 20, IMD 12, and/or external drug pump 26 may generate the delivery parameters and transmit the delivery parameters to the appropriate device.

System 30 may also be configured such that IMD 12 and external drug pump 26 use the same catheter (e.g., catheter 14) after a switch is made between the two devices. For example, external drug pump 26 may initially be coupled to catheter 14, removed from catheter 14, and then IMD 12 may be coupled to catheter 14. Alternatively, an IMD 12 can be exchanged with external drug pump 26. In addition, a catheter extension may be used in some examples during this change so that a fully implantable catheter remains within patient 1 to minimize infection. In examples where the IMD 12 and external drug pump 26 use the same catheter, the interface between the first and second fluids may occur at the location at which the connection was made to the catheter.

Figure 3:
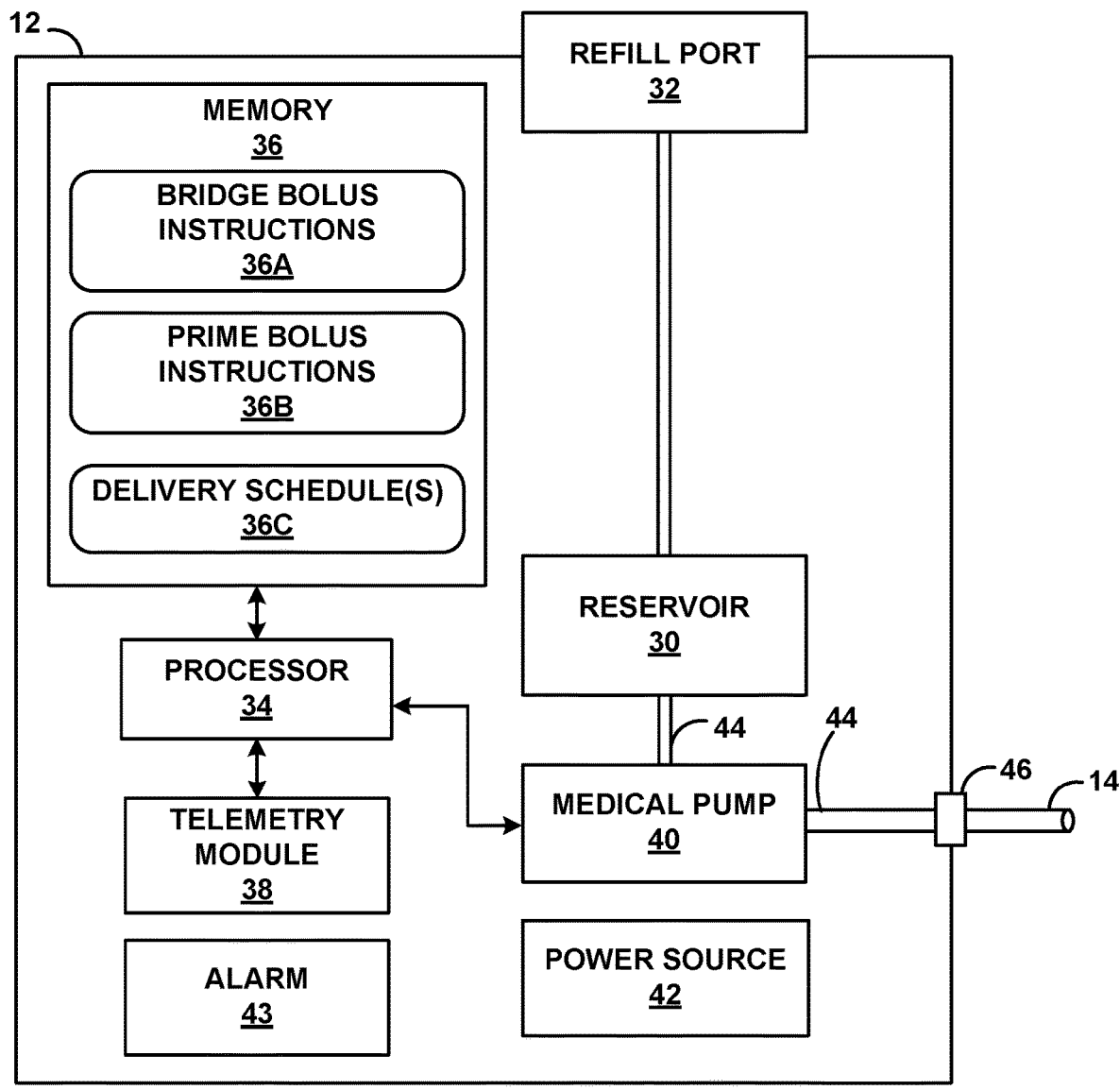
FIG. 3 is a functional block diagram of the example IMD of FIG. 1.

FIG. 3 is functional block diagram illustrating components of example IMD 12 of FIG. 1. The example IMD 12 shown in FIG. 3 includes reservoir 30, refill port 32, processor 34, memory 36, telemetry module 38, medical pump 40, power source 42, alarm 43, internal channels 44, and catheter access port (CAP) 46. IMD 12 is also shown coupled to catheter 14. IMD 12 may also include sensors that are used to determine the status of medical pump 40 or other components within IMD 12, such as a pressure sensor used to measure the pressure at the outlet of medical pump 40.

Refill port 32 provides for refilling of reservoir 30 with therapeutic fluid (e.g., a drug in liquid form). Refill port 32 may comprise a self-sealing injection port. The self-sealing injection port may include a self-sealing membrane to prevent loss of therapeutic agent delivered to reservoir 30 via refill port 32. After a delivery system, e.g., a hypodermic needle, penetrates the membrane of refill port 32, the membrane may seal shut when the delivery system is removed from refill port 32. Internal channels 44 may comprise one or more segments of tubing and/or a series of cavities that run from reservoir 30, around or through medical pump 40 to catheter access port 46. The fluid path downstream of medical pump 40 may include the internal channels 44 between medical pump 40 and catheter access port 46, catheter access port 46, and catheter 14.

Processor 34 may include one or more processors and be configured to control the operation of medical pump 40 with the aid of software instructions associated with program information that is stored in memory 36. In one example, processor 34 is configured to run the software instructions in order to control operation of IMD 12. For example, the software instructions may define one or more therapy programs (e.g., such as a drug delivery schedule) that specify the amount of a therapeutic agent (e.g., drug) that is delivered to a target tissue site within patient 1 from reservoir 30 via catheter 14, e.g., dose, the rate at which the agent is delivered, e.g., dosage rate, flow rate, and the time at which the agent will be delivered and the time interval over which the agent will be delivered, e.g., the delivery schedule for dose or doses defined by the therapy program (e.g., based on the instructions stored in memory 32). In other examples, a quantity of the therapeutic agent may be delivered, at least in part, according to one or more physiological characteristics of a patient, e.g., physiological characteristics sensed by one or more sensors (not shown) implanted within a patient as part of therapy system 10 (FIG. 1), or according to a combination of scheduled doses and physiological characteristics. In some examples, a patient may be permitted to increase or reduce one or more doses. In addition, memory 36 may include instructions regarding the determination of an initial delivery period for a transition in drug delivery as described herein.

Processor 34 can include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry.

Memory 36 may include any volatile or non-volatile media, such as a random access memory (RAM), read only memory (ROM), non-volatile RAM (NVRAM), electrically erasable programmable ROM (EEPROM), flash memory, and the like. As mentioned above, memory 36 may store program information including instructions for execution by processor 34, such as, but not limited to, therapy programs, historical therapy programs, timing programs for delivery of the therapeutic agent from reservoir 30 to catheter 14, instructions for transitioning drug delivery (e.g., delivering a prime bolus or bridge bolus) and any other information (e.g., physiological data or operating data) regarding therapy of patient 1. Memory 36 may include separate memory portions for storing instructions, patient information, therapy parameters (e.g., grouped into sets referred to as "dosing programs"), therapy adjustment information, program histories, and other categories of information such as any other data that may benefit from separate physical memory modules. Memory 36 may also include the bridge bolus instructions 36A, prime bolus instructions 36B, and delivery schedules 36C. These instructions and schedules may contain portions of or all of the data stored as bridge bolus instructions 53, prime bolus instructions 54, and delivery schedules 56 stored in memory 52 of programmer 20 described in FIG. 4. IMD 12 may receive the data of one or more of bridge bolus instructions 36A, prime bolus instructions 36B, delivery schedules 36C, and other instructions from programmer 20 as instructions that define at least a portion of therapy delivery.

Telemetry module 38 in IMD 12, as well as telemetry modules in programmers, such as external programmer 20, may accomplish communication by RF communication techniques. In addition, telemetry module 38 may communicate with programmer 20 via proximal inductive interaction of IMD 12 with external programmer 20. Processor 34 controls telemetry module 38 to send and receive information. In other examples, telemetry module 38 may also exchange data with external drug pump 26 of FIG. 1 or other devices.

Power source 42 delivers operating power to various components of IMD 12. Power source 42 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, non-rechargeable storage devices may be used for a limited period of time. As a further alternative, an external inductive power supply could transcutaneously power IMD 12 whenever measurements are needed or desired.

Medical pump 40 may be a mechanism that delivers a drug in some metered or other desired flow rate or dosage to target site 2 within patient 1 from reservoir 30 via catheter 14. Medical pump 40 may include an actuation mechanism that is electrically energized to provide a pump stroke to move fluid from reservoir 30. The actuation mechanism may comprise an electromagnetic coil and an actuator that is movable in response to electrical energization of the coil. Other actuation mechanisms may be used, such as a piezo-actuator. Medical pump 40 may be configured to deliver drug with a variety of different programmable flow rates.

Alarm 43 may include one or more components configured to convey information to patient 1 regarding therapy delivery. As examples, alarm 43 may include a speaker to provide audible signals, a vibration device configured to provide haptic feedback, and/or one or more electrodes to provide an electrical stimulus. Processor 34 may be configured to operate alarm 43 to signal an empty or near-empty reservoir 30, a malfunction of IMD 12, or when changes to flow rates or which fluid is delivered during drug transitions. Alarm 43 may thus inform patient 1 that a change in drug delivery will occur (e.g., a change in therapy program or delivery schedule, initializing a transition period with a new drug or different drug concentration, or change in flow rate). In some examples, alarm 43 may prompt patient 1 and/or the clinician to turn off delivery of drug from external drug pump 26 in response to expiration of the initial delivery period.

IMD 12 may be configured as a single housing comprising the components of FIG. 3. In other examples, control circuitry may be housed in a secondary device that communicates with a device that includes reservoir 30, medical pump 40, processors 34, and other components. The secondary device may include memory 36, one or more processors (e.g., control circuitry), and a telemetry module that directly controls the operation of IMD 12 to perform each task. In this manner, the functions described to IMD 12 herein may be performed by two or more different devices, implanted and/or external of patient 1.

Figure 4:
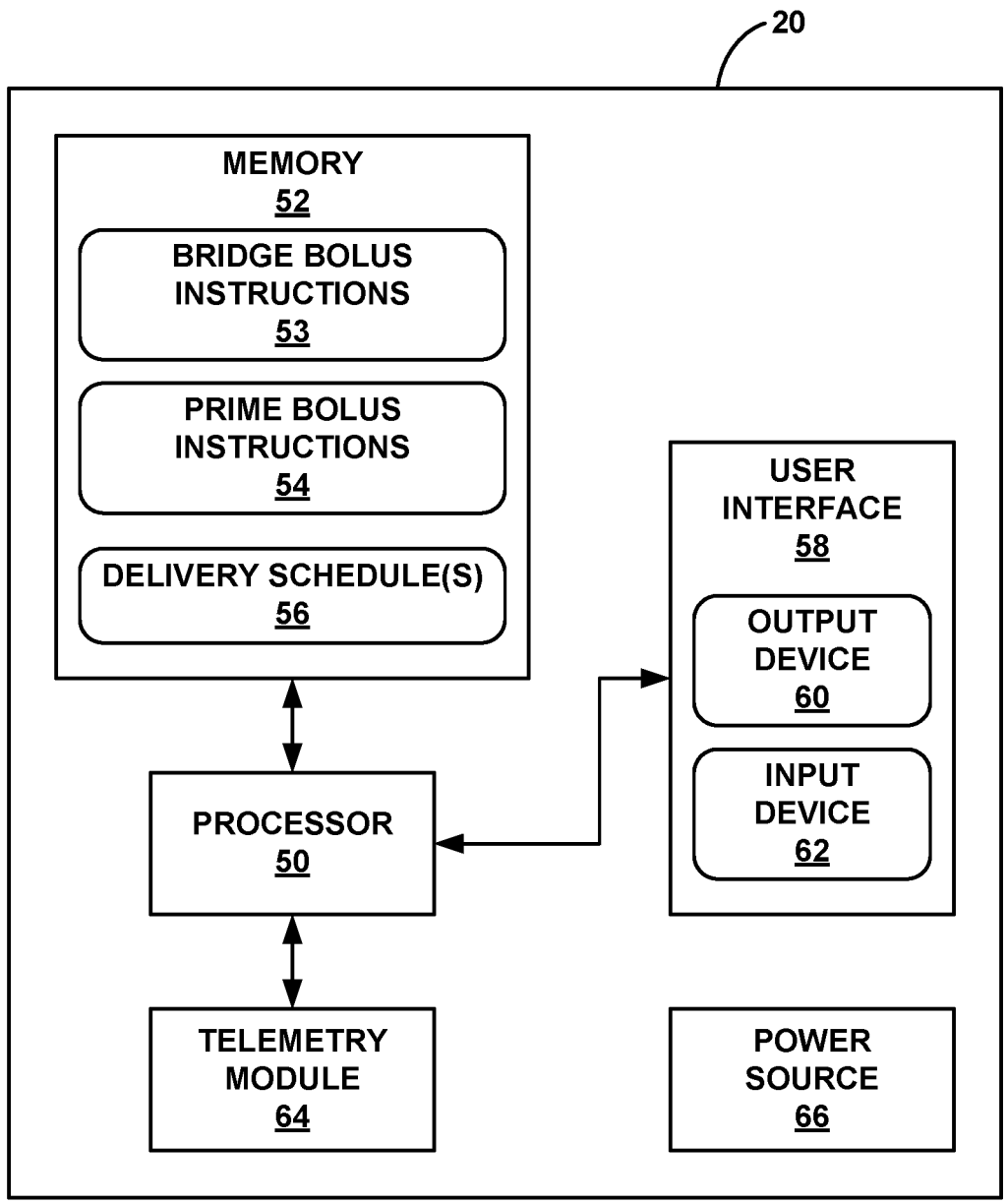
FIG. 4 is a functional block diagram of the example external programmer of FIG. 1.

FIG. 4 is a functional block diagram of example external programmer 20 of FIG. 1. Although programmer 20 may generally be described as a hand-held device, programmer 20 may be a larger portable device or a more stationary device. In addition, in other examples, programmer 20 may be included as part of an external charging device or include the functionality of an external charging device and/or a home monitoring device. As illustrated in FIG. 4, programmer 20 may include a processor 50, memory 52, user interface 58, sensor 60, telemetry module 64, and power source 66. Memory 52 may store instructions that, when executed by processor 50, cause processor 50 and external programmer 20 to provide the functionality ascribed to external programmer 20 throughout this disclosure (such as a distributed system 100 described in FIG. 6)

In general, programmer 20 comprises any suitable arrangement of hardware, alone or in combination with software and/or firmware, to perform the techniques attributed to programmer 20, and processor 50, user interface 58, and telemetry module 64 of programmer 20. In various examples, programmer 20 may include one or more processors, such as one or more microprocessors, DSPs, ASICs, FPGAs, or any other equivalent integrated or discrete logic circuitry, as well as any combinations of such components. Programmer 20 also, in various examples, may include a memory 52, such as RAM, ROM, PROM, EPROM, EEPROM, flash memory, a hard disk, a CD-ROM, or a DVD comprising executable instructions for causing the one or more processors to perform the actions attributed to them and/or store any data generated related to patient therapy. Moreover, although processor 50 and telemetry module 64 are described as separate modules, in some examples, processor 50 and telemetry module 64 are functionally integrated. In some examples, processor 50 and telemetry module 64 correspond to individual hardware units, such as ASICs, DSPs, FPGAs, or other hardware units.

Memory 52 (e.g., a storage device) may store instructions that, when executed by processor 50, cause processor 50 and programmer 20 to provide the functionality ascribed to programmer 20 throughout this disclosure. For example memory 52 may include instructions that cause processor 50 to obtain drug delivery schedules from memory, generate therapy programs and delivery schedules, receive user input and send corresponding commands to IMD 12, determine fluid delivery periods, determine flow rates for one or more fluids, or any other functionality. In addition, memory 52 may include one or more drug delivery schedules 56, where each schedule may include a therapy program or set of delivery parameters (e.g., delivery times and flow rates) that defines therapy. In some examples, delivery schedules 56 may include a set of patterns and steps that collectively define each respective delivery schedule. The data stored in memory 52 may also include information related to previous therapy sessions, previous medical devices, tables with fluid characteristics, one or more concentration profiles, or any other such information.

In the example shown in FIG. 4, memory 52 stores, among other data, bridge bolus instructions 53, prime bolus instructions 54, and delivery schedules 56 in separate memories within memory 52, separate areas within memory 52, or the same areas within memory 52. In some examples, memory 52 may also store instructions to allow patient-requested (e.g., via input) bolus delivery or other therapy changes during therapy. Each stored delivery schedule 56 defines a particular set of drug delivery parameters that may define therapy delivery from IMD 12 and/or external drug pump 26. These parameters may include drug concentrations, flow rates, times or schedules for fluid delivery, error conditions and error handing information, or any other information related to delivery of therapy to patient 1. In some examples, these delivery parameters may be contained within respective "steps" that can be added to one or more "patterns" within the respective delivery schedule. Delivery schedule 56 may be predefined and stored in memory 52, adjusted by a user, and/or generated from user input. One of more of delivery schedules 56 may be transmitted to IMD 12 and/or external drug pump 26 via wired or wireless communication.

Memory 52 may also include bridge bolus instructions 53. Bridge bolus instructions 53 may include instructions related to determining one or more parameters of a bridge bolus of drug to be delivered to patient 1 during a transition period between different drugs or different concentrations of drugs. Bridge bolus instructions 53 may include concentration profiles for one or more drugs, flow rate information for various dosages, instructions for calculating different flow rates, target dosages, fluid mixing parameters, viscosity of one or more fluids, or any other information described herein related to transitioning fluid delivery. These instructions for determining the transition period and/or flow rates may include one or more look-up tables, formulas, or algorithms, such as those described with respect to FIGS. 8A and 8B. In some examples, bridge bolus instructions 53 may also store predetermined delivery parameters generated by system 10 such as programmer 20 or IMD 12.

Memory 52 may also include prime bolus instructions 54. Prime bolus instructions 54 may include instructions related to determining one or more parameters of a prime bolus of drug to be delivered to patient 1 during a transition period in which drug is initially delivered to patient 1 from a newly implanted IMD 12 and/or catheter 14. This prime bolus may be delivered when transitioning from delivery via another device (e.g., external drug pump 26) to deliver via IMD 12. Prime bolus instructions 54 may include concentration profiles for one or more drugs, flow rate information for various dosages, instructions for calculating different flow rates, target dosages, fluid mixing parameters, viscosity of one or more fluids, and/or instructions for calculating different flow rates when delivering drug from reservoir 30 of IMD 12, for example, and the inert fluid within catheter 14. These instructions for determining the delivery periods and/or flow rates may include one or more look-up tables, formulas, or algorithms. In some examples, prime bolus instructions 54 may also store predetermined delivery parameters generated by system 10 such as programmer 20 or IMD 12. Although bridge bolus instructions 53 and prime bolus instructions 54 are described separately, similar instructions for determining flow rates and delivery periods may be applicable to both bridge bolus and prime bolus transitions.

User interface 58 may include one or more output devices 60 (e.g., a display device) and one or more input device 62. Output devices 60 may include, lights, a speaker for voice commands, a display device, such as a liquid crystal (LCD), light-emitting diode (LED), or organic light-emitting diode (OLED), printer, or another networked device. Input device 62 may include a button, keypad, pointing device, or presence-sensitive display. In some examples the display device may be a touch screen (e.g., a presence-sensitive screen). User interface 58 may be configured to display any information related to the delivery of therapy, concentration profiles, flow rates, target dosages, target prescription doses, or any other such information described herein. User interface 58 may also receive user input via input device 62. The input may be, for example, in the form of pressing a button on a keypad or selecting an icon from a touch screen. The input may select a type of drug, desired transition periods for delivering a mixed fluid, one or more patterns and steps for a delivery schedule, turn drug delivery on or off, or any other inputs related to drug delivery described herein. Programmer 20 may also receive input or data (e.g., drug delivery schedules, drug delivery parameters, fluid information, etc.) from other devices (e.g., IMD 12 or external drug pump 26) via wired or wireless connections such as those connections supported by telemetry module 64.

Telemetry module 64 may support wireless communication between IMD 12 and programmer 20 under the control of processor 50. Telemetry module 64 may also be configured to communicate with another computing device (e.g., external drug pump 26) via wireless communication techniques, or direct communication through a wired connection. In some examples, telemetry module 64 may be substantially similar to telemetry module 38 of IMD 12 described herein, providing wireless communication via an RF or proximal inductive medium. In some examples, telemetry module 64 may include one or more antennas, which may take on a variety of forms, such as one or more internal or external antennas (e.g., two or more diversity antennas). Examples of local wireless communication techniques that may be employed to facilitate communication between programmer 20 and IMD 12 including RF communication according to the 802.11 or Bluetooth specification sets or other standard or proprietary telemetry protocols.

Figure 5:
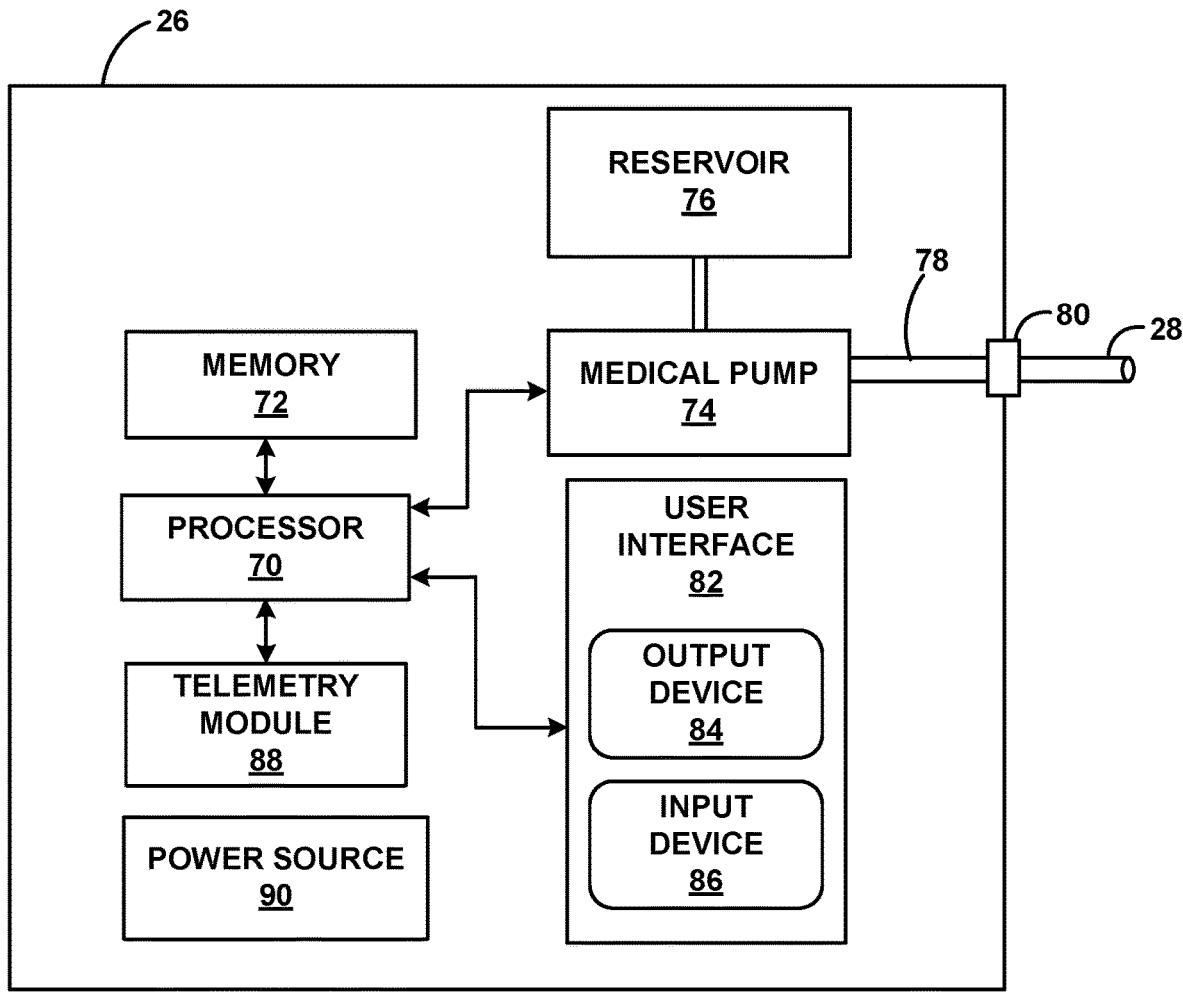
FIG. 5 is a functional block diagram of the example external drug pump of FIG. 2.

FIG. 5 is a functional block diagram of the example external drug pump 26 of FIG. 2. The example external drug pump 26 shown in FIG. 5 includes reservoir 76, processor 70, memory 72, telemetry module 88, medical pump 74, power source 90, internal channels 78, and catheter coupling 80. Medical pump 74 is also shown coupled to catheter 28. Reservoir 76 is shown as internal to, or contained within, the housing of external drug pump 26. For example, reservoir 76 may be in the form of a vial, tube, or other such system in which the therapeutic fluid and/or therapeutic agent is prepackaged and placed within the housing of external drug pump 26 and/or attached to a side of the housing. Alternatively, or additionally, reservoir 76 may be external to the housing of external drug pump 26 (e.g., in the form of a gravity fed bag, a syringe, or a cartridge) in other examples. Internal channels 78 may comprise one or more segments of tubing and/or a series of cavities that run from reservoir 76, around or through medical pump 74, to catheter coupling 80. The fluid path downstream of medical pump 74 may include internal channels 78, catheter coupling 80, and catheter 28.

Processor 70 may include one or more processors and be configured to control the operation of medical pump 74 with the aid of software instructions associated with program information that is stored in memory 72. In one example, processor 70 is configured to run the software instructions in order to control operation of external drug pump 26. For example, the software instructions may define one or more therapy programs that specify the amount of a therapeutic agent (e.g., drug) that is delivered to a target tissue site within patient 1 from reservoir 76 via catheter 28, e.g., dose, the rate at which the agent is delivered, e.g., dosage rate and/or flow rate, and the time at which the agent will be delivered and the time period over which the therapeutic agent will be delivered, e.g., the delivery schedule. In other examples, a quantity of the therapeutic agent may be delivered, at least in part, according to one or more physiological characteristics of a patient, e.g., physiological characteristics sensed by one or more sensors (not shown) implanted within a patient as part of therapy system 30 (FIG. 2), or according to a combination of scheduled doses and physiological characteristics. In some examples, a patient may be permitted to increase or reduce one or more doses. In addition, memory 72 may include instructions regarding the determination of an initial delivery period for a transition in drug delivery as described herein.

Processor 70 can include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry.

Memory 72 may include any volatile or non-volatile media, such as a random access memory (RAM), read only memory (ROM), non-volatile RAM (NVRAM), electrically erasable programmable ROM (EEPROM), flash memory, and the like. As mentioned above, memory 72 may store program information including instructions for execution by processor 70, such as, but not limited to, drug delivery schedules, historical delivery schedules, timing programs for delivery of the therapeutic agent from reservoir 76 to catheter 14, instructions for transitioning drug delivery (e.g., delivering a prime bolus or bridge bolus) and any other information regarding therapy of patient 1, such as data generated or received related to therapy delivery. Memory 72 may include separate memory portions for storing instructions, patient information, delivery parameters (e.g., grouped into sets referred to as "dosing programs" or delivery schedules), therapy adjustment information, program histories, and other categories of information such as any other data that may benefit from separate physical memory modules. For example, memory 72 may be similar to memory 52 of IMD 12 and include drug delivery schedules, bridge bolus instructions, and/or prime bolus instructions.

Telemetry module 88 in external drug pump 26, as well as telemetry modules in programmers, such as external programmer 20, may accomplish communication by RF communication techniques. In addition, or alternatively, telemetry module 88 may communicate with IMD 12 via proximal inductive interaction of external drug pump 26 with external programmer 20. Processor 70 controls telemetry module 88 to send and receive information. In other examples, telemetry module 88 may also exchange data with external programmer 20 of FIG. 1 or other devices. In other examples, wired protocols may be used to exchange information with programmer 20.

Power source 90 delivers operating power to various components of external drug pump 26. Power source 90 may include a small rechargeable or non-rechargeable battery and a power generation circuit to produce the operating power. Alternatively, power source 90 may be a power converter configured to receive power from an external outlet or power supply.

Medical pump 74 may be a mechanism that delivers a drug in some metered or other desired flow rate or dosage to target site 2 within patient 1 from reservoir 76 via catheter 28. Target site 2 may be the same site for catheter 28 and catheter 14 as shown in the example of FIG. 2. Medical pump 74 may include an actuation mechanism that is electrically energized to provide a pump stroke to move fluid from reservoir 76. The actuation mechanism may comprise an electromagnetic coil and an actuator that is movable in response to electrical energization of the coil. Other actuation mechanisms may be used, such as a piezoactuator. Medical pump 74 may be configured to deliver drug with a variety of different programmable flow rates. Medical pump 74 may be similar to medical pump 40 of IMD 12.

External drug pump 26 may also include user interface 82. User interface 82 may include one or more output device 84 (e.g., a display device) and one or more input device 86. Output device 84 may include, lights, a speaker for voice commands, a display device, such as a liquid crystal (LCD), light-emitting diode (LED), or organic light-emitting diode (OLED). Input device 86 may include a button, keypad, pointing device, or presence-sensitive display. In some examples, the display device may be a touch screen (e.g., a presence-sensitive screen). User interface 82 may be configured to display any information related to the delivery of therapy, concentration profiles, flow rates, target prescription doses, delivery periods, or any other such information described herein. User interface 82 may also receive user input via input device 86. The input may be, for example, in the form of pressing a button on a keypad or selecting an icon from a touch screen. The input may select a desired time period for delivering any fluids, flow rates, one or more drugs, one or more delivery schedules, turn drug delivery on or off, or any other inputs related to drug delivery described herein.

Figure 6:
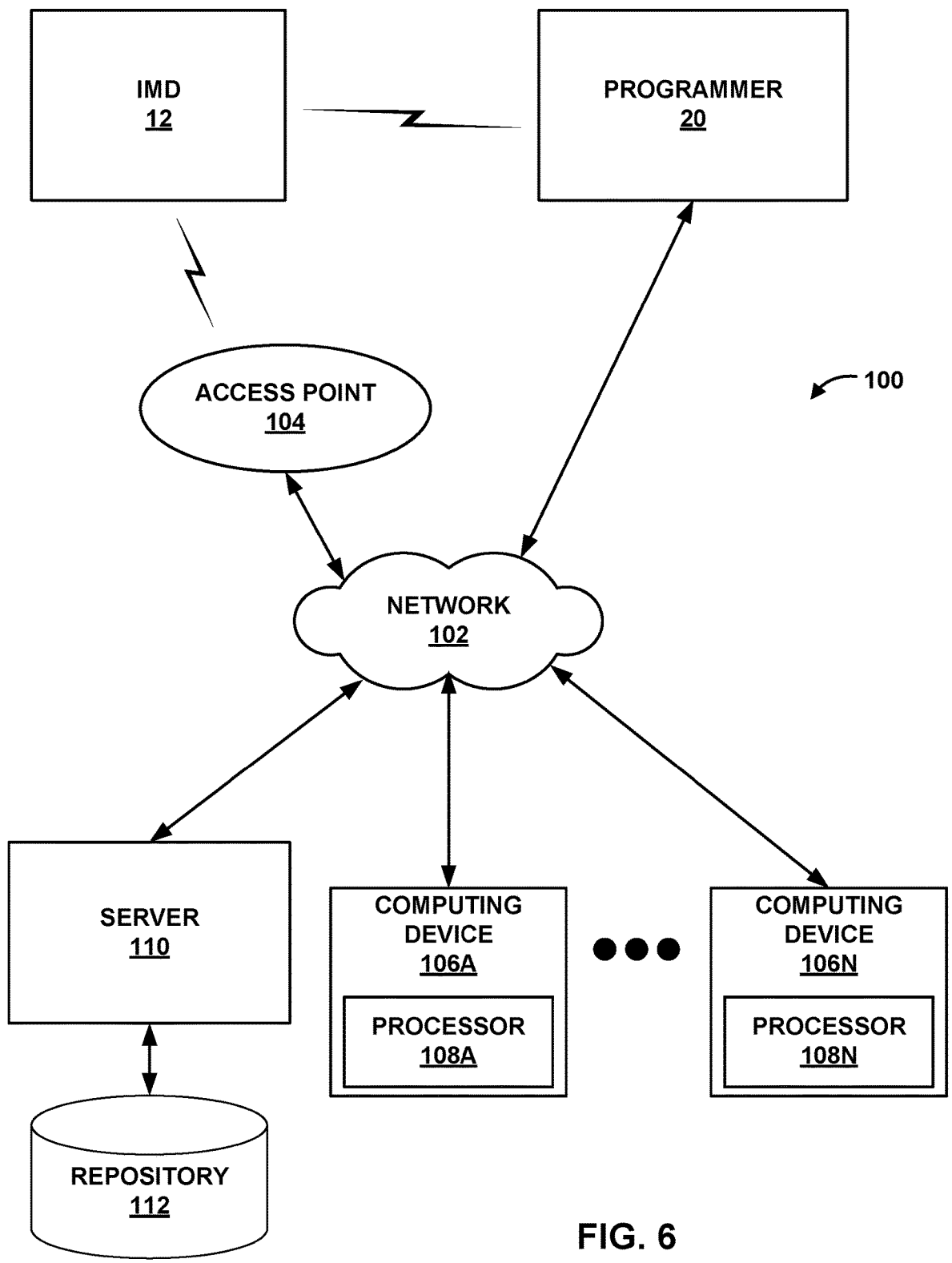
FIG. 6 is a block diagram illustrating an example system that includes a networked server coupled to an IMD and one or more computing devices via a network.

FIG. 6 is a block diagram illustrating an example system 100 that includes a networked server 110 coupled to IMD 12 and one or more computing devices 106 via network 102. As shown in FIG. 6, server 110 (e.g., a networked external computing device) and one or more computing devices 106A-106N (collectively "computing devices 106") that are coupled to the IMD 12 and programmer 20 shown in FIG. 1 via a network 102. Each of computing devices 106 may include a respective processor 108. Network 102 can be generally used to transmit therapy programs, concentration profiles, target transition doses, initial delivery periods, sensed patient data, or any other information between IMD 12, programmer 20, external drug pump 26, server 110 and/or computing devices 106.

In some examples, IMD 12 and/or programmer 20 may transmit flow rates, concentration profiles, and/or delivery periods to server 110 and/or computing devices 106 for processing and determination of the different flow rates during the drug transition. Calculating the flow rates, or generating the concentration profile for specific parameters of the drug delivery, may be computationally intensive and require additional power in some examples. In addition, server 110 and/or computing devices 106 may generate the concentration profile based on experimental data or other data points. Offloading tasks like these to server 110, for example, may provide for faster determination (e.g., calculation) of parameters and prevent excess drain of battery power from programmer 20 and/or IMD 12. Once server 110 determines the initial delivery period, for example, server 110 may transmit the set of values back to programmer 20 and/or IMD 12.

In other examples, the information transmitted by IMD 12 may allow a clinician or other healthcare professional to monitor patient therapy delivery status and/or program therapy delivery remotely. In some examples, IMD 12 may use a telemetry module to communicate with programmer 20 via a first wireless (or inductive) connection, and to communicate with access point 104 via a second wireless (or inductive) connection, e.g., at different times or at the same time (such as using a duty cycle for both connections). In the example of FIG. 6, access point 104, programmer 20, server 110 and computing devices 106 are interconnected, and able to communicate with each other through network 102. In some cases, one or more of access point 104, programmer 20, server 110 and computing devices 106 may be coupled to network 102 via one or more wireless connections. IMD 12, programmer 20, server 110, and computing devices 106 may each comprise one or more processors, such as one or more microprocessors, DSPs, ASICs, FPGAs, programmable logic circuitry, or the like, that may perform various functions and operations, such as those described herein.

Access point 104 may comprise a device that connects to network 102 via any of a variety of connections, such as telephone dial-up, digital subscriber line (DSL), cable modem connections, cellular, or satellite connections. In other examples, access point 104 may be coupled to network 102 through different forms of connections, including wired or wireless connections. In some examples, access point 104 may be co-located with patient 12 and may comprise one or more programming units and/or computing devices (e.g., one or more monitoring units) that may perform various functions and operations described herein. For example, access point 104 may include a home-monitoring unit that is co-located with patient 12 and that may monitor the activity of IMD 12. In some examples, server 110 or computing devices 106 may control or perform any of the various functions or operations described herein.

In some cases, server 110 may be configured to provide a secure storage site (e.g., via repository 112) for therapy parameters, concentration profiles, target prescribed doses target transition doses, initial delivery periods, sensed data, or other data that has been collected and generated from IMD 12 and/or programmer 20. Network 102 may comprise a local area network, wide area network, or global network, such as the Internet. The system of FIG. 6 may be implemented, in some aspects, with general network technology and functionality similar to that provide by the Medtronic CareLink® Network developed by Medtronic, Inc., of Minneapolis, Minn.

Figure 7A:
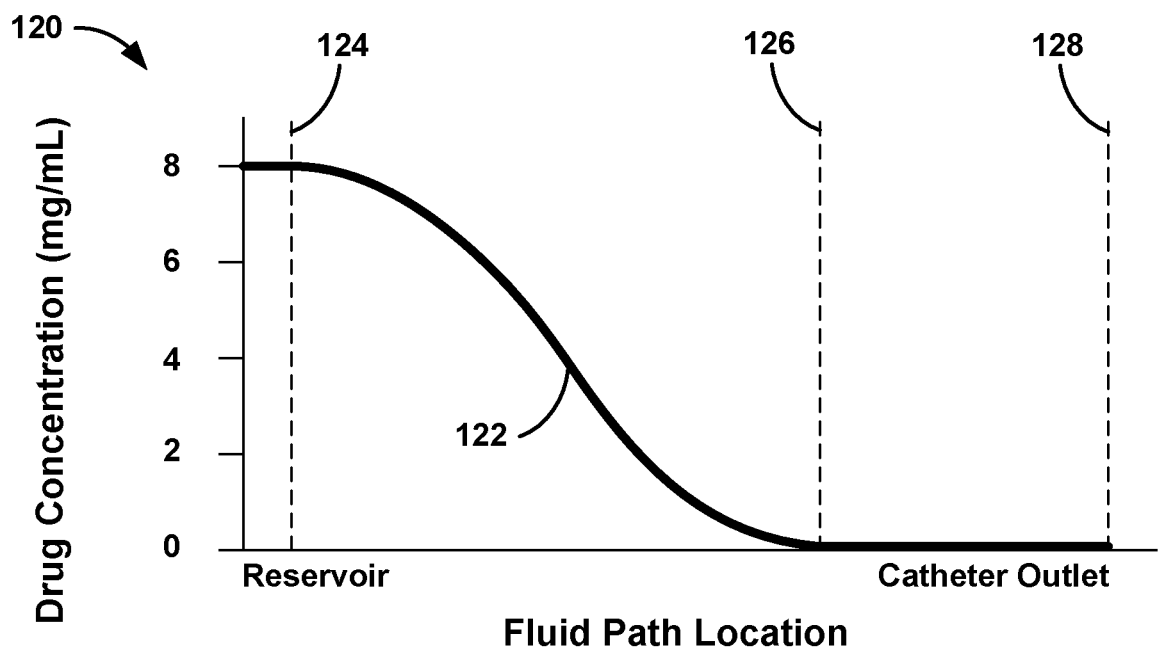
FIGS. 7A, 7B, and 7C are graphs illustrating example changes in concentration of a drug caused by mixing of two different fluids in a fluid path.
Figure 7B:
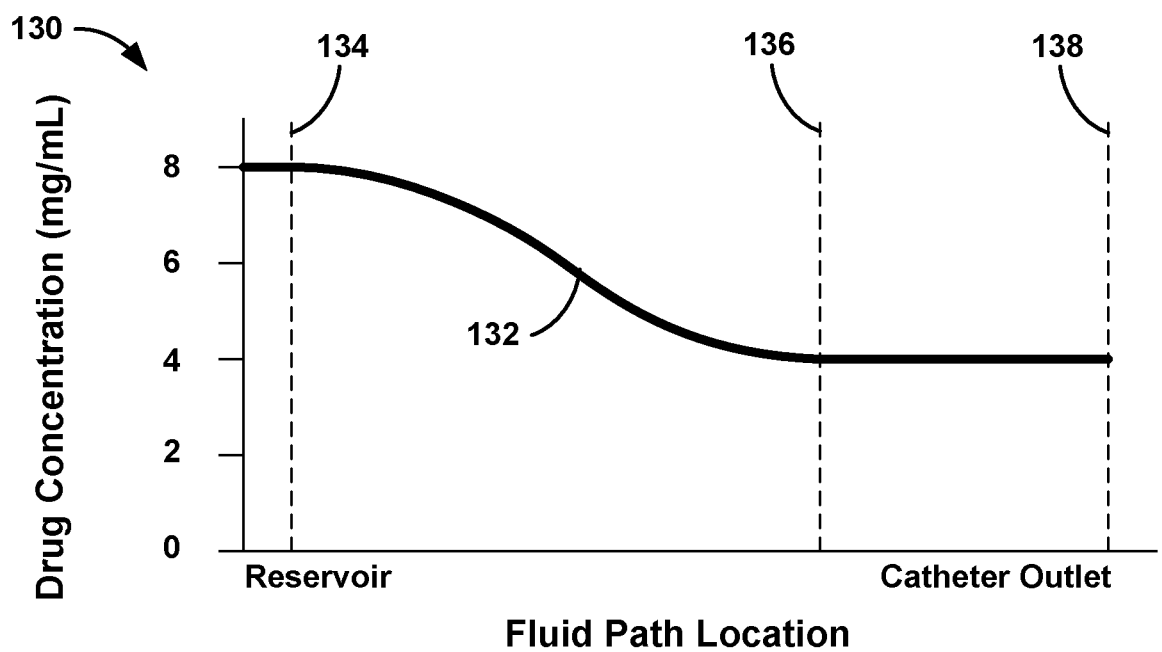
Figure 7C:
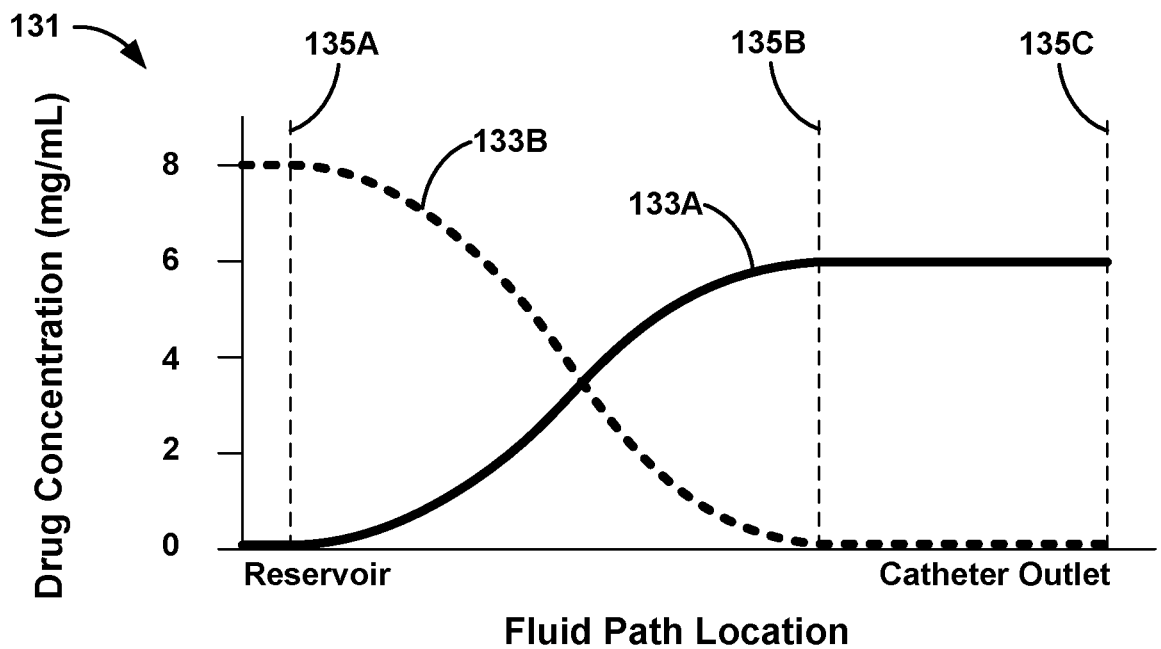

FIGS. 7A, 7B, and 7C are graphs illustrating example changes in concentration of a drug caused by mixing of two different fluids in a fluid path. The graphs of FIGS. 7A, 7B, and 7C may thus illustrate example concentration profiles. Some concentration profiles may include equations or other mathematical representations that estimate the gradient of a therapeutic agent within a mixed fluid. FIG. 7A may be representative of a concentration profile for a prime bolus and FIG. 7B may be representative of a concentration profile for a bridge bolus. FIG. 7C may be representative of concentration profiles for two different therapeutic agents within two different fluids. When two fluids come in contact with each other, the boundary between the fluids may not remain highly defined. Instead, respective portions of the two fluids mix with each other or undergo some diffusion at the boundary. The result is a gradient, or profile, that represents the interface between the two fluids. In other words, there is some volume of fluid at the interface that contains a portion of both fluids. The concentration profile of the drug within this interface can estimate the concentration of the drug at various positions within the fluid.

As shown in FIG. 7A, graph 120 illustrates the change in drug concentration with respect to the location within the fluid path (e.g., passages and catheter 14 downstream from reservoir 30 of IMD 12) for a newly implanted IMD 12. Concentration curve 122 indicates the concentration of the drug in mg/mL along the length of the fluid path, such as between the reservoir (e.g., reservoir 30 and the outlet of catheter 14). Between locations 126 and 128, the fluid may be the first fluid having a consistent concentration of approximately zero mg/mL. The first fluid between locations 126 and 128 may thus be an inert fluid for which a prime bolus is delivered to transition to the second fluid stored within the reservoir. The second fluid at the reservoir may have a concentration of approximately 8.0 mg/mL upstream of location 124.

The fluid volume between locations 124 and 126 may include the mixed fluid that contains a mixture of the first fluid and the second fluid. This mixed fluid may be caused by mixing and diffusion of the therapeutic agent from the second fluid to the first fluid. In other words, the fluid between locations 124 and 126 may define the interface between the first and second fluids. The distance between locations 124 and 126 may vary based on the types of fluid, therapeutic agent, temperature, fluid viscosities, cross-sectional area of the fluid path, concentration profiles, fluid pressure, and/or other variables. One or more of these factors may be detected by one or more sensors. In some examples, a device (e.g., IMD 12, external drug pump 26, or programmer 20) may update calculations regarding the third fluid (e.g., fluid volume between locations 124 and 126, duration of time the third fluid will be delivered, etc.) in real-time or near real-time based on data from one or more sensors. The extent of mixing shown in FIG. 7A may not be to scale. In other words, the mixed fluid may be a relatively large portion (e.g., greater than 50 percent) of the total fluid within the fluid path, a very small portion (e.g., less than one percent) of the total fluid within the fluid path, or any portion in between.

The representation of concentration curve 122 may be indicative of the fluid concentration that exits catheter 14. In other words, the maximum volume of mixed fluid may occur when the mixed fluid reaches the output of catheter 14. When the second fluid is first introduced to catheter 14 from reservoir 30, no time has elapsed to permit any mixing. However, as the second fluid is forced out of the fluid path and against the first fluid over time, increased mixing may cause the volume of the mixed fluid to increase until the mixed fluid exits catheter 14. Therefore, the concentration profile may estimate the concentration gradient as the fluid exits from catheter 14.

Conversely, the concept shown in FIG. 7A may apply in the reverse situation in which an inert fluid is the second fluid being delivered after the first fluid, including a drug, is delivered to a patient. In other words, the concentration between locations 126 and 128 will be the concentration of the drug, and the concentration before location 124 is zero because an inert fluid has been added to the reservoir to be delivered to the patient. Such an inert fluid may be used to wean a patient off of the drug previously delivered to the patient.

As shown in FIG. 7B, graph 130 illustrates the change in drug concentration with respect to the location within the fluid path (e.g., passages and catheter 14 downstream from reservoir 30 of IMD 12) for a refilled reservoir 30 of IMD 12 with a different concentration of a therapeutic agent. Concentration curve 132 indicates the concentration of the drug in mg/mL along the length of the fluid path, such as between the reservoir (e.g., reservoir 30 and the outlet of catheter 14. Between locations 136 and 138, the fluid may be the first fluid having a concentration of the therapeutic agent of approximately 4.0 mg/mL. The first fluid between locations 126 and 128 may thus be the current or previous fluid for which a bridge bolus is delivered to transition to the second fluid stored within the reservoir. The second fluid at the reservoir may have a concentration of approximately 8.0 mg/mL upstream of location 134.

Similar to graph 120 of FIG. 7A, the fluid volume between locations 134 and 136 may include the mixed fluid that contains a mixture of the first fluid and the second fluid. This mixed fluid may be caused by mixing and diffusion of the higher concentration of therapeutic agent from the second fluid to the lower concentration of the therapeutic agent in the first fluid. In other words, the fluid between locations 134 and 136 may define the interface between the first and second fluids. The distance between locations 134 and 136 may vary based on the types of fluid, therapeutic agent, temperature, fluid viscosities, cross-sectional area of the fluid path, concentration profile, fluid pressure, and possibly other variables. The extent of mixing shown in FIG. 7B may not be to scale. In other words, the mixed fluid may be a relatively large portion (e.g., greater than 50 percent) of the total fluid within the fluid path, a very small portion (e.g., less than one percent) of the total fluid within the fluid path, or any portion in between.

The representation of concentration curve 132 may be indicative of the fluid concentration that exits catheter 14. In other words, the maximum volume of mixed fluid may occur when the mixed fluid reaches the output of catheter 14. When the second fluid is first introduced to catheter 14 from reservoir 30, no time has elapsed to permit any mixing. However, as the second fluid is forced out of the fluid path and against the first fluid over time, increased mixing may cause the volume of the mixed fluid to increase until the mixed fluid exits catheter 14. Therefore, the concentration profile may estimate the concentration gradient as the fluid exits from catheter 14. In examples in which the transition involves changing concentration from a higher concentration to a lower concentration, the concentration curve 132 may be reversed.

As shown in graphs 120 and 130 of FIGS. 7A and 7B, a larger difference between concentrations of the first and second fluid may result in a larger gradient within the mixed fluid. In some examples, larger concentration differences between the first and second fluids may result in a larger volume of mixed fluid. Therefore, the concentration profile may account for the extent of mixing, the dimensions of the fluid path, and any other variables may affect the volume of mixed fluid that exits catheter 14. The concentration curves 122 and 132 may be used to generate respective concentration profiles that represent such curves. A device (e.g., IMD 12 or programmer 20) may use a concentration profile to determine one or more flow rates for delivering the mixed fluid to patient 1.

As shown in FIG. 7C, graph 131 illustrates the change in drug concentrations of two different drugs with respect to the location within the fluid path (e.g., passages and catheter 14 downstream from reservoir 30 of IMD 12) for a refilled reservoir 30 of IMD 12 with a fluid having a different therapeutic agent than the therapeutic agent previously delivered. In this manner, concentrations curves 133A and 133B indicate the respective concentrations of a therapeutic agent within the fluid as they mix together with respect to the location within the fluid path. Between locations 135B and 135C, the fluid may be the first fluid having a concentration of the first therapeutic agent of approximately 6.0 mg/mL. The first fluid between locations 135B and 135C may thus be the current or previous fluid for which a bridge bolus is delivered to transition to the second fluid and second therapeutic agent stored within the reservoir. The second fluid at the reservoir may have a concentration of approximately 8.0 mg/mL of the second therapeutic agent upstream of location 135A.

The fluid volume between locations 135A and 135B may include the mixed fluid that contains a mixture of the first fluid and the second fluid, and the respective first and second therapeutic agents. This mixed fluid may be caused by mixing and diffusion of the higher concentration of therapeutic agent from the second fluid to the lower concentration of the therapeutic agent in the first fluid. In other words, the fluid between locations 135A and 135B may define the interface between the first and second fluids and may include portions of both of the first and second therapeutic agents. The distance between locations 135A and 135B may vary based on the types of fluid, therapeutic agent, temperature, fluid viscosities, cross-sectional area of the fluid path, concentration profile, fluid pressure, and possibly other variables. The extent of mixing shown in FIG. 7C may not be to scale. In other words, the mixed fluid may be a relatively large portion (e.g., greater than 50 percent) of the total fluid within the fluid path, a very small portion (e.g., less than one percent) of the total fluid within the fluid path, or any portion in between.

The representation of concentration curve 133A may be indicative of the first therapeutic agent concentration that exits in catheter 14. The representation of concentration curve 133B may be indicative of the second therapeutic agent concentration that exits in catheter 14. The portion of mixed fluid (i.e., the third fluid) between locations 135A and 135B may thus include varying concentrations of both the first and second therapeutic agents. For example, as the location moves upstream from the catheter outlet (and fluid is delivered to the patient), concentration profile 133A indicates that the concentration of the first therapeutic agent decreases and concentration profile 133B indicates that the concentration of the second therapeutic agent increases. When the second fluid is first introduced to catheter 14 from reservoir 30, no time has elapsed to permit any mixing. However, as the second fluid is forced out of the fluid path and against the first fluid over time, increased mixing may cause the volume of the mixed fluid to increase (e.g., the distance between locations 135A and 135B) until the mixed fluid exits catheter 14. Therefore, the concentration profiles 133A and 133B may estimate the concentration gradient as the fluid exits from catheter 14.

As described herein, the flow rates of the mixed fluid may be determined based on the first fluid flow rate and/or the second fluid flow rate. In some examples, wherein a drug delivery schedule having various flow rates in the schedule is used to deliver the first or second fluid, the one or more determined flow rates for the mixed fluid may be selected based on one or more flow rates of the drug delivery schedules. For example, one or more processors may obtain the last flow rate of the drug delivery schedule to deliver the first fluid and the first flow rate of the drug delivery schedule to deliver the second fluid. In other words, these obtained flow rates may be the flow rates adjacent to the mixed fluid or that lead into and out of the mixed fluid delivery. The processors may then determine one or more flow rates for the mixed fluid based on the obtained flow rates from the drug delivery schedule(s). For example, the processors may calculate an average flow rate between the obtained flow rates for the transition of the mixed fluid. In other examples, a ramped or step-wise flow rate schedule may be generated with the obtained flow rates from the drug delivery schedule(s) as start and end points for the flow rate schedule.

In some examples, the flow rates for the mixed fluid may be calculated by a processor based on a ratio of the flow rate that would have been used by each drug delivery schedule for the respective drug over the delivery period of the mixed fluid. In other words, the concentration profile of each fluid may be used to specify a percentage of drug concentration over time or volume. This percentage may be multiplied by the flow rate of the fluid that would have been used to deliver the fluid as if the fluid had a full concentration of drug at that time. The flow rate percentages for each fluid may then be added together to define the flow rate for the mixed fluid at that time. In this manner, flow rates and/or drug delivery schedules may be generated for the mixed fluid based on drug delivery schedules of the first and/or second fluid.

For the example of FIG. 7C with different therapeutic agents, the calculation of flow rates for the mixed fluid may be similar to that of the calculation for mixed fluid having different concentrations of the same therapeutic agent. However, the flow rates may be adjusted based on the therapeutic agents involved. In other words, the flow rates for the mixed fluid may not just be an average of the flow rates used for non-mixed fluid. For example, if the first therapeutic agent poses a greater risk to overdosing, the system may determine flow rates closer to the flow rate of the first therapeutic agent until the mixed fluid has been delivered. In this manner, the flow rate for the mixed fluid or change in flow rates for the mixed fluid may be unsymmetrical with respect to the difference between flow rates of the full concentration fluids or the time between the start and end of the mixed fluid delivery.

Figure 7D:
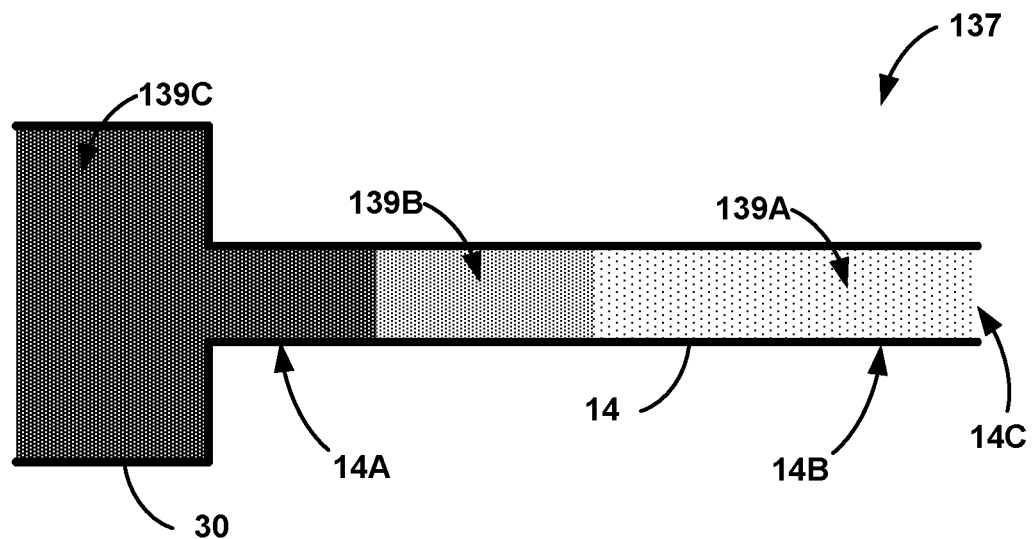
FIG. 7D is a conceptual illustration of example fluid mixing within a fluid path of fluid delivery device.

FIG. 7D is a conceptual illustration of example fluid mixing within an example fluid path 137 of a fluid delivery device (e.g., IMD 12 and catheter 14). Fluid path 137 may be defined by catheter 14, reservoir 30, and/or other passages or channels between reservoir 30 and catheter 14. As described herein, fluid path 137 may include three different fluids. The first fluid 139A may or may not include a therapeutic agent at a certain concentration. The second fluid 139C may include the same therapeutic agent at the same concentration, the same therapeutic agent at a different concentration, or a different therapeutic agent. The third fluid 139B represents the mixture of both first fluid 139A and second fluid 139C. In other words, third fluid 139B may represent the interface between first fluid 139A initially located at the distal portion 14B of catheter 14 and second fluid 139C located at the proximal portion 14A of catheter 14.

When second fluid 139C is initially introduced to first fluid 139A, the volume of third fluid 139B may be effectively zero. However, as time elapses and fluid moves distally toward catheter outlet 14C, the volume of third fluid 139B may increase. As described herein, the concentration profile and/or volume of the third fluid 139B may represent the fluid as it exits catheter outlet 14C. In other words, the concentration profile may be indicative of the mixing within catheter 14, but the concentration profile may approximate the status of third fluid 139B as the patient would perceive it through the dosage received.

Figure 8A:
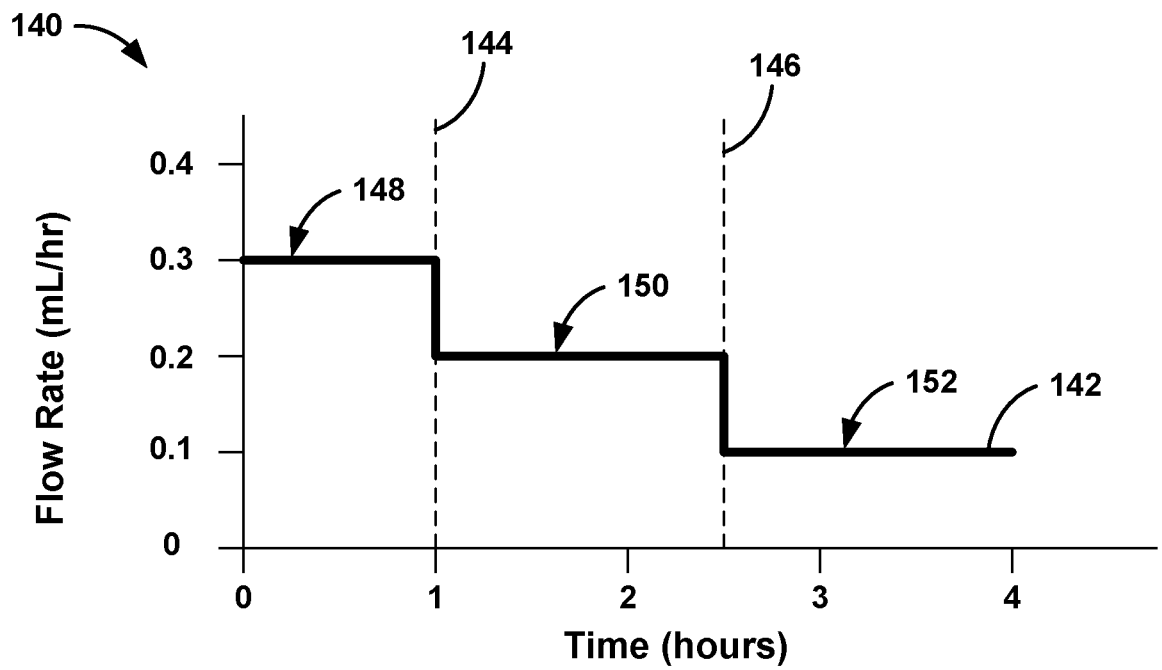
FIGS. 8A, 8B, and 8C are graphs illustrating example flow rates for transitioning between two different concentrations of respective fluids.
Figure 8B:
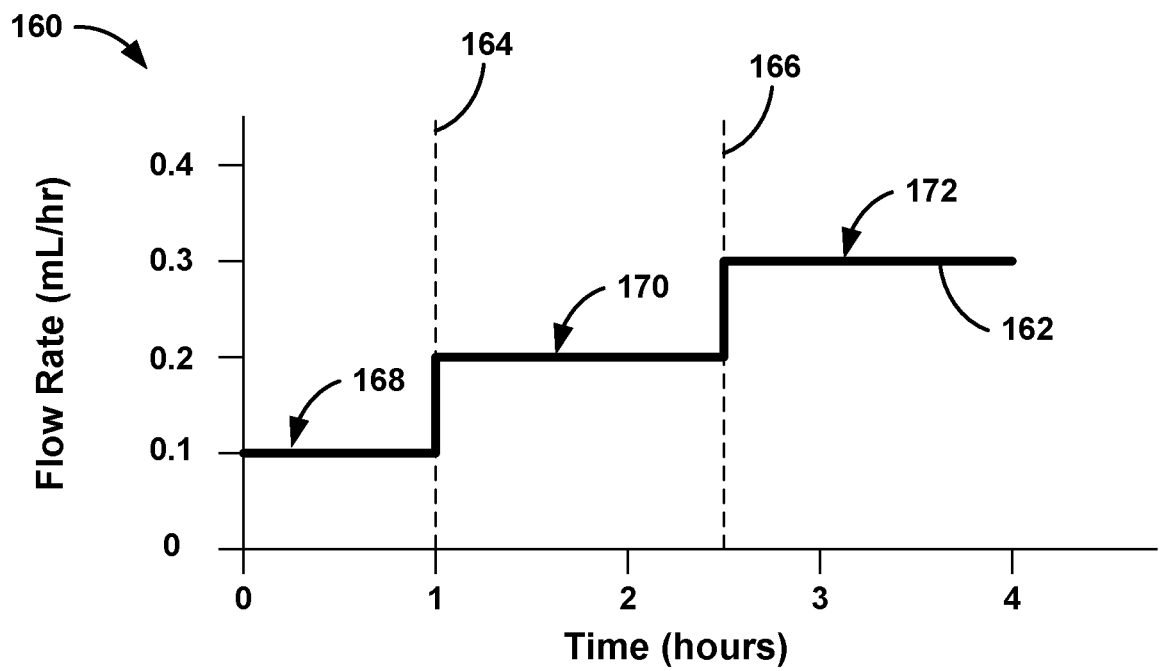
Figure 8C:
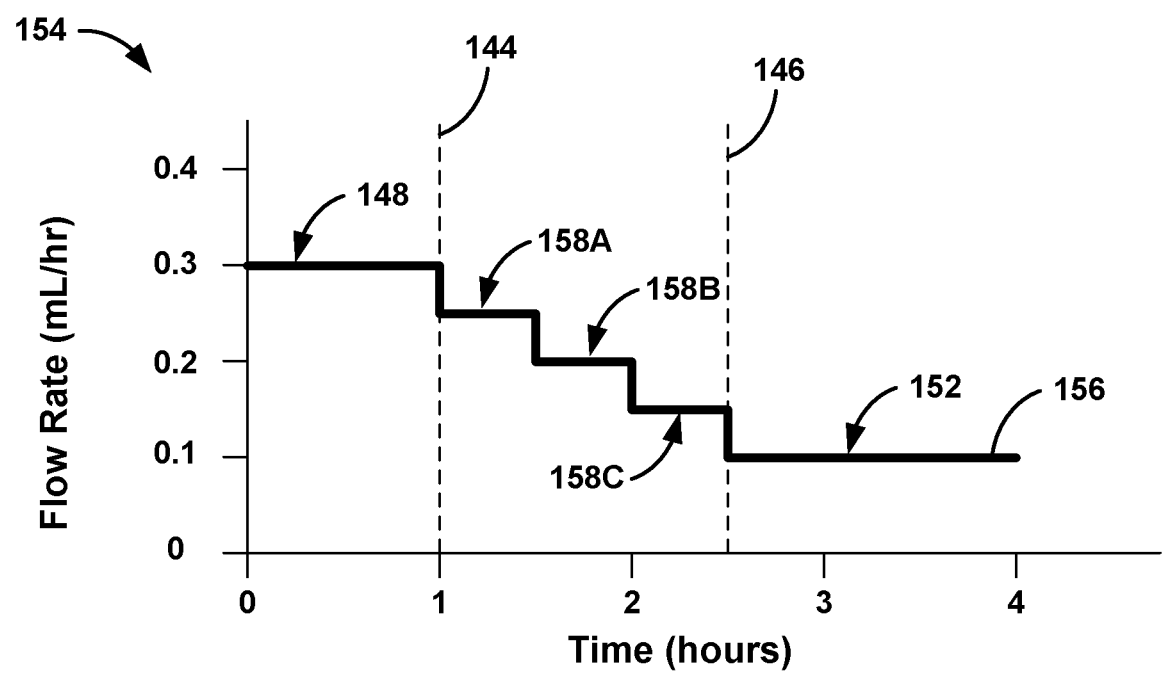

FIGS. 8A, 8B, and 8C are graphs illustrating example flow rates for transitioning between two different concentrations of respective fluids. Graph 140 of FIG. 8A may illustrate example flow rates used to deliver fluid during a transition from fluid with a low concentration of a therapeutic fluid to a fluid with a high concentration of the therapeutic fluid. In contrast, graph 160 of FIG. 8B may illustrate example flow rates used to deliver fluid during a transition from fluid with a high concentration of a therapeutic fluid to a fluid with a low concentration of the therapeutic fluid. Although FIGS. 8A, 8B, and 8C are described with respect to changing between fluids of different concentrations of the same therapeutic agent, similar flow rate changes may be used to change between a fluid without a therapeutic agent and a fluid with a therapeutic agent or change between fluids having one or more different therapeutic agents.

As shown in FIG. 8A, graph 140 illustrates the changes in flow rate 142 over time as IMD 12 transitions between a first fluid, the mixed fluid, and the second fluid. Flow rate value 148 may indicate the flow rate (e.g., 0.3 mL/hr) used to deliver the first fluid at a lower concentration than the second fluid. At time marker 144, the volume of the first fluid may be completely delivered from catheter 14 and the mixed fluid begins to be delivered from catheter 14. Therefore, the flow rate is decreased (e.g., by IMD 12 or programmer 20) to flow rate value 150 to accommodate the increasing concentration of the mixed fluid. Flow rate value 150 may be selected to be an average of the flow rate for the first fluid and the second fluid, such as approximately 0.2 mL/hr. The mixed fluid may then be delivered at flow rate value 150 until the mixed fluid has been completely delivered at time marker 146. At time marker 146, the flow rate may again be decreased to flow rate value 152 of approximately 0.1 mL/hr. The duration of time between time markers 144 and 146 may be calculated by IMD 12 or programmer 20 based on the determined volume of the mixed fluid (e.g., from the concentration profile) and flow rate value 150. The flow rate values 148 and 152 may be flow rates specified by the drug delivery schedule for each of the first and second fluids.

As shown in FIG. 8B, graph 160 illustrates the changes in flow rate 162 over time as IMD 12 transitions between a first fluid, the mixed fluid, and the second fluid. Flow rate value 168 may indicate the flow rate (e.g., 0.1 mL/hr) used to deliver the first fluid at a higher concentration than the second fluid. At time marker 164, the volume of the first fluid may be completely delivered from catheter 14 and the mixed fluid begins to be delivered from catheter 14. Therefore, the flow rate is increased (e.g., by IMD 12 or programmer 20) to flow rate value 170 to accommodate the decreasing concentration of the mixed fluid. Flow rate value 170 may be selected to be an average of the flow rate for the first fluid and the second fluid, such as approximately 0.2 mL/hr. The mixed fluid may then be delivered at flow rate value 170 until the mixed fluid has been completely delivered at time marker 166. At time marker 166, the flow rate may again be increased to flow rate value 172 of approximately 0.3 mL/hr. The duration of time between time markers 164 and 166 may be calculated by IMD 12 or programmer 20 based on the determined volume of the mixed fluid (e.g., from the concentration profile) and flow rate value 170. The flow rate values 168 and 172 may be flow rates specified by the drug delivery schedule for each of the first and second fluids.

The flow rate values shown in FIGS. 8A and 8B are examples and may vary in other examples. The determined flow rate values for each of the mixed fluids are shown as an average of the flow rates for the first and second fluids. However, the determined flow rates may be less than or more than an average in other examples. These non-average flow rates for the mixed fluids may be selected based on an unsymmetrical concentration profile and/or a preference for erring on the side of underdosing or overdosing. For example, if overdosing from the therapeutic agent creates more side effects than underdosing, IMD 12 or programmer 20 may determine the flow rate for the mixed fluid to be lower than the average flow rate to deliver less dosage during the transition. Alternatively, if underdosing from the therapeutic agent creates more side effects than overdosing, IMD 12 or programmer 20 may determine the flow rate for the mixed fluid to be higher than the average flow rate to deliver greater dosage during the transition.

In other examples, IMD 12 and/or programmer 20 may employ two or more different flow rates may to deliver the mixed fluid to patient 1. Multiple different flow rates may allow the flow rate to more closely follow the changes in concentration indicated by the concentration profile of the therapeutic agent. These different flow rates for the mixed fluid may be referred to as a dynamic flow rate for the mixed fluid. FIG. 8C includes graph 154 that illustrates an example of delivering the mixed fluid (i.e., the third fluid) at multiple different flow rates. Graph 154 may be similar to graph 140 of FIG. 8A; however, flow rate value 150 has been segmented to three different flow rate values 158A, 158B, and 158C (collectively "flow rate values 158"). Therefore, flow rate 156 changes between time markers 144 and 146 multiple times in a step-wise function to achieve the different flow rate values 158. These different flow rate values 158 may more closely match the concentration profile of the mixed fluid. These multiple flow rate values may also apply to examples such as the example of FIG. 8B. In some examples, a drug delivery schedule may incorporate different flow rates of the mixed fluid to deliver accurate dosing of drug during the transition between the first and second fluids.

Flow rate values 158 are shown to change an equal amount between each flow rate value 158 and flow rate values 148 and 152. Flow rate values 158 are also shown as changing over equal time periods. However, flow rate values 158 may change using unequal rate changes and/or over unequal time periods between time markers 144 and 146. In other examples, Flow rate values 158 may instead form a continuous curve without steps or with steps (e.g., small changes in flow rate values and small time periods) small enough to nearly match a continuous curve. Flow rate values 158 may thus be modeled or described by one or more equations specifying the flow rate as a function of time and/or volume. Such equations may include variables such as concentration of one or more therapeutic agents, one or more flow rates, viscosities of one or more fluids, and a drug delivery schedule (e.g., time or volume dependent delivery schedule). One or more sensors (e.g., sensors of IMD 12) may detect values of one or more of these variables such as flow rate, viscosity, concentration, or any other drug mixing characteristics.

In some examples, the flow rate values for delivering fluid before, during, or after the transition period as shown in FIGS. 8A and 8B may be selected or defined based on drug delivery schedules specific for the type of fluid (e.g., the first, second, or mixture of the two fluids). In this manner, IMD 12 may control fluid delivery according to the respective drug delivery schedule until time or volume tracking indicates a different fluid has reached the outlet of the catheter. At that time, IMD 12 may switch to a different drug delivery schedule (or just a new flow rate) specific for the new fluid that has reached the outlet of the catheter. For example, in the context of FIG. 8A, IMD 12 may control fluid delivery at flow rate 148 (or two or more different flow rates) according to a drug delivery schedule for the first fluid. At time marker 144 indicative of a change to the mixed third fluid, IMD 12 may control fluid delivery at flow rate 150 (which may or may not include two or more different flow rates). At time marker 146 indicative to the fluid being the second fluid, IMD 12 may again switch to the drug delivery schedule for the second fluid such that flow rate value 152 may actually include one or more flow rate values according to a drug delivery schedule for the second fluid. As described herein, time markers 144 and 146 may be determined based on tracking time of delivery or volume of delivered fluid. This application of one or more drug delivery schedules to the transitions shown in FIG. 8A may also be used to define the flow rates of example FIG. 8B.

In some examples, the one or more flow rates for the mixed fluid (e.g., flow rate values 150 or 170) may be calculated based on one or more drug delivery schedules for the first and/or second fluids that make up the third mixed fluid. For example, in the context of FIG. 8A, IMD 12 (or programmer 20 or another device) may select the last flow rate value prior to time marker 144 and the first flow rate value that will be used to deliver fluid in response to reaching time marker 146. IMD 12 may then average these two flow rate values to determine flow rate value 150. In addition, IMD 12 may generate, based on the last flow rate value prior to time marker 144 and the first flow rate value subsequent to time marker 146, two or more flow rate values for delivery of the mixed fluid between time markers 144 and 146. These multiple flow rate values 150 may include iteratively increasing or decreasing flow rate values for equal time periods between time markers 144 and 146. Alternatively, the time periods for the different flow rate values 150 may be selected to more closely match the concentration profile of the mixed fluid (e.g., smaller time periods close to time markers 144 and 146 and larger time periods in the middle to accommodate non-linear changes in drug concentration between time markers 144 and 146).

Figure 9:
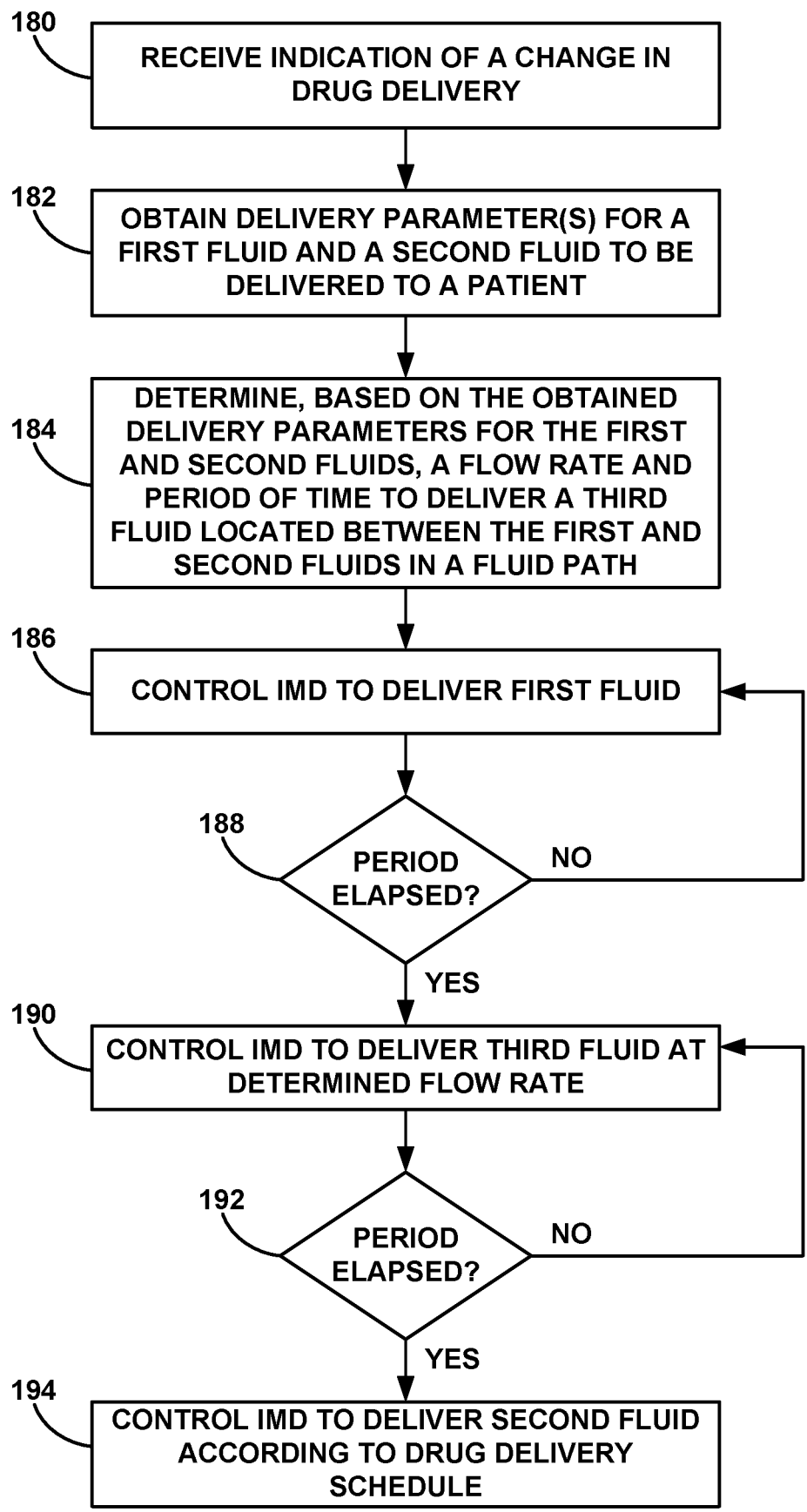
FIG. 9 is a flow diagram of an example process for determining a flow rate for delivering a fluid containing a mixture of two different fluids to a patient.

FIG. 9 is a flow diagram of an example process for determining a flow rate for delivering a fluid containing a mixture of two different fluids to a patient. Although FIG. 9 will be described with respect to processor 34 of IMD 12, similar processes would be performed by processor 50 and programmer 20, processor 80 and external drug pump 26, and/or server 110. Other sets of devices may also be used in other examples. The process of FIG. 9 may be applicable to any drug delivery transitions, such as transitions between two different drug sources and/or transitions between two different drug concentrations.

As shown in FIG. 9, processor 34 of IMD 12 may receive an indication of a change in drug delivery (180). The indication may be a signal received from another device (e.g., programmer 20) or a sensor signal that has detected fluid refill in reservoir 30, for example. Processor 34 may then obtain delivery parameters for the first fluid (e.g., the fluid within catheter 14) and the second fluid (e.g., the fluid within reservoir 30) to be delivered to patient 1 (182). The delivery parameters may include respective flow rates, delivery periods, concentrations, or any other delivery parameters (such as fluid characteristics that may affect delivery of the fluid). Based on the obtained delivery parameters for the first and second fluids, processor 34 may determine the flow rate and period of time to deliver the third fluid (e.g., the mixed fluid) located between the first and second fluids in the fluid path of system 10 (184). In some examples, processor 34 may also use a concentration profile to determine the volume of the mixed fluid and the delivery period required to deliver the mixed fluid to patient 1 at the determined flow rate.

Using the obtained delivery parameters of the first fluid, processor 34 may control medical pump 40 of IMD 12 to deliver the first fluid to patient 1 (186). If the delivery period for the first fluid has not elapsed ("NO" branch of block 188), processor 34 may continue to control delivery of the first fluid (186). If the delivery period for the first fluid has elapsed ("YES" branch of block 188), processor 34 may control medical pump 40 to deliver the third fluid at the determined flow rate (190). If the delivery period for the third fluid has not elapsed ("NO" branch of block 192), processor 34 may continue to control delivery of the third fluid (190). If the delivery period for the third fluid has elapsed ("YES" branch of block 192), processor 34 may control medical pump 40 to deliver the second fluid according to the flow rate of the drug delivery schedule for the second fluid (194). The delivery period described herein, such as the delivery period in blocks 188 and 192, may be a period tracked by time of fluid delivery or a period tracked by the volume of fluid delivered.

The process of FIG. 9 may be simplified from other examples. For example, the delivery of the first and second fluids may occur over different flow rates and delivery periods until the volume of each fluid has been completely delivered. In this manner, processor 34 may track the volume of delivered fluid to determine when to switch flow rates during the transition from the first to second fluids. In addition, processor 34 may control medical pump 40 to deliver the third fluid mixture (e.g., the delivery of fluid at block 190) at two or more different flow rates selected according to different portions of the concentration profile of the mixed fluid. For example, the different flow rates for delivering the third fluid may form an iteratively increasing or iteratively decreasing ramp to transition between the flow rates of the first and second fluids. In other examples, the process of FIG. 9 may be changed to accommodate continuous changes in flow rate (e.g., very small changes in flow rate over very changes in time). In this manner, blocks 190 and 192 may be replaced with a control loop for delivering fluid at a certain flow rate and changing the flow rate when the small change in time has elapsed.

Figure 10:
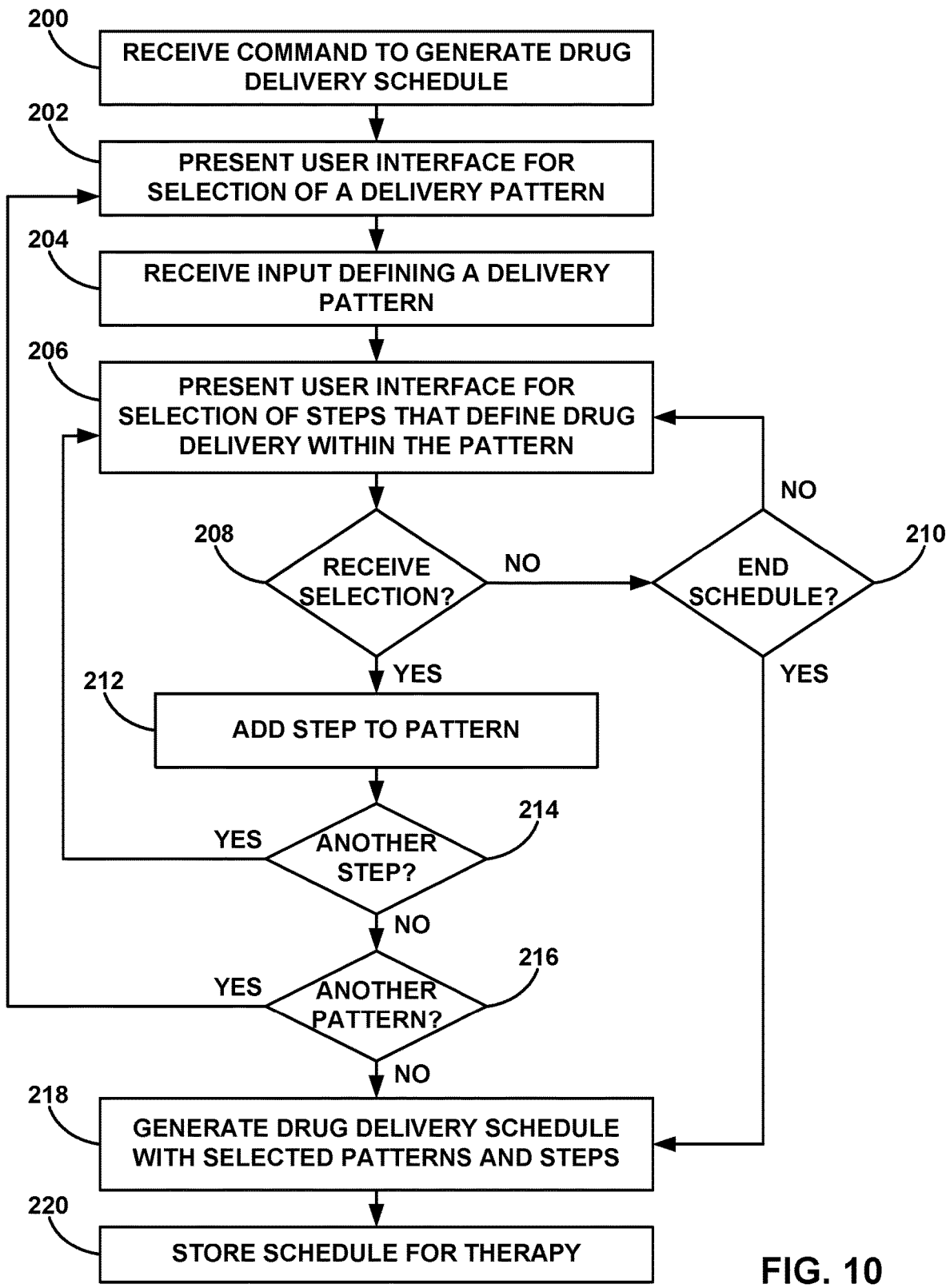
FIG. 10 is a flow diagram of an example process for generating a drug delivery schedule for delivering a drug to a patient.

FIG. 10 is a flow diagram of an example process for generating a drug delivery schedule for delivering a drug to a patient. Although FIG. 10 will be described with respect to processor 50 of programmer 20, similar processes would be performed by processor 34 and IMD 12, processor 80 and external drug pump 26, and/or server 110. Other sets of devices may also be used in other examples. The process of FIG. 10 may be applicable to any drug delivery schedule, such as schedules involving single concentrations of a therapeutic agent or transitions between two different drug sources and/or transitions between two different drug concentrations.

A drug delivery schedule may be generated using a variety of different "patterns" and "steps" that together define the delivery of fluid from IMD 12 over time. Instead of requiring the drug delivery schedule to be managed in a calendar-like framework, programmer 20 and IMD 12 may facilitate flexible programming by allowing a user to populate a number of different patterns with a number of different steps defining therapy. In other words, each pattern may define a time period in which drug delivery occurs, and each step within the respective pattern may define the delivery parameters for controlling the delivery of fluid to patient 1, such as flow rate and duration of time for providing the flow rate. In this manner, each pattern may point to one or more different steps to populate the delivery schedule during the time of each pattern. After the user defines each pattern and the respective steps of each pattern, system 10 may generate the drug delivery schedule.

As shown in the example of FIG. 10, processor 50 may receive a command to generate a drug delivery schedule (200). The command may be an initial programming command when implanting a new IMD 12, an indication of refilling reservoir 30, or user input requesting a new or updated drug delivery schedule. Processor 50 may then control output device 60 to present a user interface for selection of a delivery pattern for the delivery schedule (202). The pattern may define a period of time in which drug may be delivered during the schedule. Input device 62, and processor 50, may then receive user input defining a delivery pattern (204). Processor 50 may then control output device 60 to present the user interface for selection of one or more steps that define the drug delivery within the selected pattern (206).

If processor 50 does not receive any selection of a step ("NO" branch of block 208), processors 50 may check to determine if the selection of patterns and steps for the schedule has ended (210). If the schedule is not complete ("NO" branch of block 210), processor 50 may continue to control output device 60 to present the user interface (206). If the schedule is complete ("YES" branch of block 210), processor 50 may generate the drug delivery schedule with the selected patterns and steps (218).

If processor 50 receives a selection of a step ("YES" branch of block 208), processor 50 adds the step to the selected pattern (212). If another step is to be added ("YES" branch of block 214), processor 50 may continue to control output device 60 to present the user interface (206). If another step is not to be added to the current pattern ("NO" branch of block 214), processor 50 checks to determine if another pattern is to be added to the delivery schedule (216). If another pattern is to be added to the schedule ("YES" branch of block 216), processor 50 controls output device 60 to present the user interface for selection of another pattern (202). If no further pattern is to be added to the schedule ("NO" branch of block 216), processor 50 may generate the drug delivery schedule with the selected patterns and respective selective steps (218). Processor 50 may then store the generated drug delivery schedule for future therapy (220). Processor 50 may, in some examples, transmit the generated drug delivery schedule to IMD 12 to define delivery therapy. In other examples, processor 50 may present a comprehensive user interface configured to present a plurality of patterns and steps and receive multiple selections in any order desired by the user. Therefore, programmer 20 may support a variety of different processes for selecting patterns and steps and generating corresponding drug delivery schedules.

In some examples, the drug delivery schedule may be generated using one or more tables that define portions of the delivery schedule. As described below, Tables 1-5 provide details regarding a drug delivery schedule, such as example patterns and steps used to define the therapy from a drug delivery schedule. Other examples may provide alternative constraints with different number of patterns, steps, or structure of the schedule. Tables 1-5 are directed to delivery of drug therapy and possible bridges between different concentrations of a therapeutic agent (e.g., a bridge bolus), but similar tables may be used to define a prime bolus or other transitions as well. Each of the items within Tables 1-5 may be defined from user input.

Table 1 describes an example schedule structure. The schedule structure provides the framework for defining each drug delivery schedule (e.g., a flexible drug delivery schedule) using different patterns and steps, starting times, and information regarding the fluid path for drug transitions. The drug delivery schedule may be established for each fluid and, in some examples, for the mixed fluid occurring at the interface between a first and second fluid. The schedule may incorporate instructions for all fluids when transitioning between fluids or be separate for each fluid and indicating where to start and stop for each schedule. "Schedule Header" provides information related to the type of schedule as described further in Table 2. "Schedule Programming Time" may define the clock used to track time for the schedule. "Step slots" define each of the steps that define drug delivery for each of the "pattern slots" and are further described in Table 3. There may be "n" number of slots for respective steps. The number of steps may be between 10 steps and 100 steps in some examples. In one example, the schedule may have 32 step slots. However, fewer than 10 steps or greater than 100 steps may also be defined in other examples. "Pattern slots" define each of the patterns that may be used within the schedule and are further described in Table 4. There may be "m" number of slots for respective patterns. Example number of pattern slots may be between 1 to 20 pattern slots. However, more pattern slots may be used in some examples. An example schedule may use 6 pattern slots.

TABLE 1

| | |
|---|---|
| Schedule Header | Schedule Table Header (see Table 2) |
| Schedule Programming Time | This may be based on the pump internal time or the programmer time or a combination of both |
| Step slots | Step specification (see Table 3) for 'n' slots. |
| Pattern slots | Pattern specification (see Table 4). 'm' slots. 5-20 patterns may be used in some example, but any other number of pattern slots may be used in other examples. |
| Schedule start point index | Pointer to start of prescription table (see Table 5) |
| Bridge start point index | Pointer to location to go to after completion of bridging (e.g., transition between fluids) (see Table 5) |
| Bridge Length | Time to do bridge (minutes) |
| Bridge Volume | Volume in transparent bridge if using Volume |
| Table Integrity Data | Data used to maintain and verify integrity of table (any scheme including but not limited to cyclic redundancy checks and signatures and/or any other checks) |

Table 1 also includes "schedule start point index" that defines a pointer to indicate where in the schedule (e.g., which pattern and step) drug delivery should begin, as further explained in Table 5. "Bridge start point index" is also detailed in Table 5 and provides a pointer that indicates the location within the schedule (e.g., a specific pattern and step within the pattern) to start delivery after completion of a bridge transition from a change in drug concentration. In examples in which there is only one transition between two different schedules (e.g., no transition flow rates for the mixed fluid) only on Bridge start point index may be used. In other examples where three schedules are used (e.g., a schedule also used to define delivery for the mixed fluid), two start point indexes may be used, one to specify the location to go when starting the schedule for the mixed fluid (e.g., time markers 144 and 164 of respective FIGS. 8A and 8B) and one to specify the location to go when starting the schedule for the second fluid after completion of the bridging (e.g., time markers 146 and 166 of respective FIGS. 8A and 8B). In addition, two bridge volumes and/or two bridge lengths may be used for the three schedules to specify how long each of the first two schedules should be used prior to ending with the drug delivery schedule of the second fluid. "Bridge length" may indicate the time for transitioning between two different concentrations of fluid, which can be used when time has been selected to define the transition period. "Bridge volume" may indicate the volume of fluid needed to provide a bridge between two different concentrations of fluid. The bridge volume may define the volume of the fluid path from the exit of the pump, through any passages of IMD 12, and the catheter before the fluid would reach the patient. In other words, the bridge volume may be tracked by calculating fluid delivery (e.g., using a known volume of pump delivery, such as the number and volume of pump strokes, or using one or more sensors that sense the volume of fluid leaving catheter 12 (e.g., a flow rate sensor). "Table integrity data" may define the data that is used to maintain and verify the integrity of the drug delivery schedule (e.g., any drug delivery schedule described herein) and provide any needed error handling.

Table 2 provides details regarding the drug delivery schedule header. The header may include a "prescription ID" that defines the name of identifier of the specific drug delivery schedule. This information may be specific to the schedule and/or patient for which the schedule has been prescribed. "Infusion configuration" details may include user or device selected specifications regarding the schedule. This information may define the schedule type (e.g., a simple continuous schedule or a flexible or complex prescription), whether or not a bridge between different fluids (e.g., different drug concentrations or different drugs) should be transparent to the user (e.g., maintaining schedule details during transition) or revert to default delivery parameters for the transition period, and whether the system will track time or volume of delivered fluid when transitioning between two different drug concentrations. In situations in which a drug delivery schedule is used to deliver the mixed fluid, the bridge type for each of the different transitions between schedules may be specified in Table 3. Table 3 may also be changed to accommodate more than two schedule transitions (e.g., transitions between three schedules) such as each transitioning specifying the bridge and type of bridge to use in controlling delivery during the transition. In some examples, time or volume tracking of the fluid being delivered may also be used by a medical device to gradually introduce delivery a new therapeutic agent or gradually terminate delivery of an old therapeutic agent.

TABLE 2

| Prescription ID | |
|---|---|
| Infusion Configuration | Prescription type simple continuous flex/complex prescription Bridge simple flow for bridge schedule used for bridge Bridge Type Time Volume |

Table 3 provides details regarding slot structure of each step. "Step ID" may provide identification of the unique step used to provide drug delivery. "Step start delay duration" indicates the time for which the step can be delayed during which a background flow rate can be used for the specific pattern. "Step duration" may indicate the duration of time for which drug delivery will occur for the specific step. In some examples, the duration of time may be set to an unlimited time period. "Rate" indicates the flow rate at which the medical pump will deliver fluid to the patient.

TABLE 3

| | |
|---|---|
| Step ID | ID of the current Step |
| Step Start Delay Duration | Time for which step can be delayed for which pattern background rate is used |
| Step Duration | Step Duration Time including, an option to run this step forever |
| Rate | Rate at which to deliver this step |

Table 4 provides details regarding the pattern structure of each schedule. "Pattern status" indicates whether the pattern is currently active of inactive for the drug delivery schedule. "Pattern iterations" indicates the number of iterations for the specific pattern, e.g., three iterations if the pattern is used for three days of the calendar week or any number of iterations needed to establish the overall schedule with one or more different pattern. "Number of steps in this pattern" indicates the number of steps that are used within the pattern. "Pattern start delay" indicates the time to delay starting of a pattern, where a default background flow rate is used instead during the delay. "Pattern background rate" defines the default flow rate to use during a step delay within the pattern. "List of steps in this pattern" identifies each of the steps that are used within the pattern. Each of the Step IDs of the respective steps may be listed so that IMD 12, for example, may select the appropriate step when drug is delivered according to this pattern. "Next pattern to jump to" defines a list of patterns to which drug delivery will proceed when the current pattern is completed. At the completion of the current pattern, the drug delivery schedule may not always jump to the same next pattern. Instead, the schedule may jump to different next patterns based on which iteration of the pattern is being used.

TABLE 4

| | |
|---|---|
| Pattern Status | Pattern Active or Inactive |
| Pattern Iterations | Number of iterations for this pattern within the schedule |
| Number of Steps in Pattern | Number of Steps in this Pattern |
| Pattern Start Delay | Time to delay for starting a pattern - Pattern Background Rate used |
| Pattern Background Rate | Pattern Background rate for this pattern (used by step delay within the step or by Pattern Start Delay) |
| List of Steps in this Pattern | List of steps making up this pattern by referencing the Step ID that make up this pattern |
| Next Pattern To Jump To | A list of patterns to jump to on completion of the current pattern that it circulates through based on how programmed. |

As one example, the drug delivery schedule may include patterns used for each of the seven day calendar week, Monday through Sunday. Pattern 1 may be used for Monday, Thursday, and Saturday. Pattern 2 may be used for Tuesday and Wednesday. Pattern 3 may be used for Friday and Sunday. Therefore, pattern 1 may have three different entries for jumping to the correct pattern after each of the pattern iterations. In other words, Pattern 1 will jump to Pattern 2 after the Monday iteration, Pattern 3 after the Thursday iteration, and Pattern 3 again after the Saturday iteration.

Table 5 provides details regarding pointers within the schedule for a certain event, such as initial starting of the drug delivery schedule, after transition from one drug concentration to another (e.g., a bridge bolus), or following a clinician appointment. "Pattern jump parameters" may indicate the pattern number of which to start, the iterations left for the starting pattern, and the starting step to use within the starting pattern. "Step delay duration remaining" may provide the time left for the selected starting step of the pattern to begin. If the remaining duration is zero, the schedule may immediately proceed to the step. "Step duration remaining" indicates the time remaining for the delay of the selected step. If the drug delivery schedule has been interrupted for an event, these times may be updated such that the drug delivery schedule may be restarted where the schedule left off.

TABLE 5

| | |
|---|---|
| Pattern Jump Parameters | Pattern Number to start at Pattern number of iterations left Pattern step pointer to start with |
| Step Delay Duration Remaining | Number of minutes left for the selected step start delay |
| Step Duration Remaining | Number of minutes left for the selected step delay |

Table 5 is shown for the example in which the schedule transitions between two different fluids. However, Table 5 may be modified to accommodate additional transitions such as from the first fluid to the mixed fluid and from the mixed fluid to the second fluid. In this manner, Table 5 may be used to specify the pattern jump parameters for each of the transitions (e.g., changing from the first fluid to the mixed fluid and changing from the mixed fluid to the second fluid). In this manner, the pattern to start at or how many iterations left in each pattern may be specified for when the change is made to a different fluid. In this manner, patterns of one or more steps may be used to define the delivery of the first fluid, the mixed fluid (third fluid), and/or the second fluid to the patient.

When delivering fluid from IMD 12 or any other device, the respective device may track delivery in order to have a record of where delivery stopped after an unexpected event, pump problem, memory error, or any other issue that may interrupt regularly scheduled drug delivery. In this manner, system 10 may provide one or more different features that accommodate faults during the delivery of therapy and attempt to maintain therapy for patient 1. For example, one or more devices within a delivery system (e.g., IMD 12 and/or programmer 20) may store a copy of the drug delivery schedule in a non-volatile memory of IMD 12 and/or programmer 20. If the volatile memory of IMD 12 is corrupted, for example, an original copy of the drug delivery schedule may be retrieved and used for continued therapy.

In another example, IMD 12 and/or programmer 20 may track the time and/or volume of fluid delivered during delivery by the drug delivery schedule and/or the transition between two different fluids. For example, if fluid flow is disrupted during a transition period, IMD 12 may retain the known delivered volume of each fluid so that the amount of fluid, and which fluid, within catheter 14 is known. When normal delivery of fluid is restarted, IMD 12 may resume delivery of fluid using the known volume of fluid that remains to be delivered from catheter 14. For example, IMD 12 may resume the drug delivery schedule or drug transition based on the known volume of a specific fluid that has already been delivered. In this manner, tracking time or volume for delivery may accommodate unexpected interruptions in the delivery of fluid using the drug delivery schedule. In addition, IMD 12 and/or programmer 20 may provide alerts or other instructions to a user identifying the amount of fluid delivered, the point in the transition between fluids, and any other information that may indicate the dosage that patient 1 has received prior to and/or during the fault condition.

Corruption in memory or of any instructions may be detected using techniques such as cyclic redundancy checks (CRC). When any errors are detected, IMD 12 or programmer 20 may take specific actions to correct the error and resume safe delivery of drug to patient 1. By storing another copy of the drug delivery schedule and/or tracking the volume of fluid actually delivered to the patient, regularly scheduled therapy may resume and maintain the drug dosage expected by the patient. In this regard, IMD 12 and/or programmer 20 may maintain a drug delivery history that records all used flow rates, respective fluids and drugs, and times, as therapy progresses through a transition period and/or a drug delivery schedule.

Figure 11:
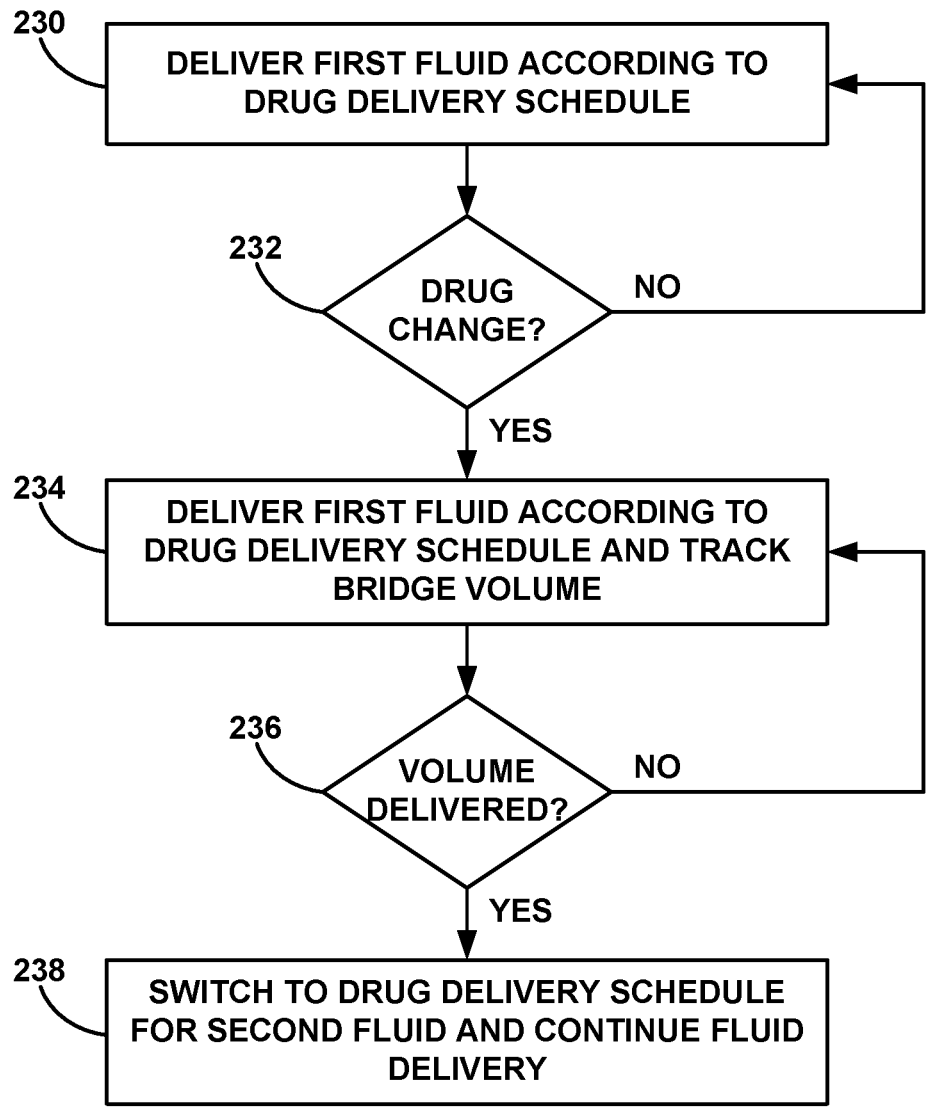
FIG. 11 is a flow diagram of an example process for maintaining a drug delivery schedule after drug change has been performed.

FIG. 11 is a flow diagram of an example process for maintaining a drug delivery schedule after drug change has been performed. Although FIG. 11 will be described with respect to processor 34 of IMD 12, similar processes would be performed by processor 50 and programmer 20, processor 80 and external drug pump 26, and/or server 110. Other sets of devices may also be used in other examples. The process of FIG. 11 may be applicable to any drug delivery schedule, such as schedules involving single concentrations of a therapeutic agent (e.g., ramping up delivery of a single drug or ramping down delivery of a single drug to minimize effects of the change in delivery to the patient) or transitions between two different drug sources and/or transitions between two different drug concentrations.

As shown in FIG. 11, processor 34 may control the delivery of a first fluid according to a drug delivery schedule generated for the first fluid (230). The first fluid may contain one or more therapeutic agents at certain concentrations. The drug delivery schedule may have one or more patterns and one or more steps for each of the patterns as described herein (e.g., a flexible drug delivery schedule). In this manner, the drug delivery schedule may define various flow rates and times for delivering fluid from IMD 12. Processor 34 may also monitor for any drug change (232). A drug change may be refilling reservoir 30 with a second fluid having a different concentration of the same therapeutic agent and/or a different therapeutic agent. Processor 34 may determine the change occurred via one or more sensors (e.g., pressure or flow sensors) or by receiving an indication of the drug change from programmer 20. If processor 34 determines that there has been no change to the drug ("NO" branch of block 232), processor 34 may continue to deliver the first fluid according to the drug delivery schedule (230).

If processor 34 determines that a drug change has occurred ("YES" branch of block 232), processor 34 may continue to deliver the first fluid according to the drug delivery schedule and start monitoring the volume of the bridge of fluid still remaining in the catheter 14 (234). The volume of fluid may be monitored to determine how much of the first fluid still remains within the system before the second fluid reaches the outlet of catheter 14. The volume may be determined based on dimensions of the fluid path downstream of the reservoir 30. Processor 34 may then track the time and flow rate to determine the volume of the first fluid remaining in IMD 12 and/or catheter 14. In other examples, one or more sensors may sense the volume of fluid that remains within the system or has exited the catheter. In some examples, the volume may be determined assuming no mixing at the interface between the first and second fluids. In other examples, the mixed fluid volume may be determined and the volume for which to deliver at the original drug delivery schedule may be determined to not include any of the mixed fluid, include all of the mixed fluid, or include a portion of the mixed fluid, depending on instructions defining the transition to the next drug delivery schedule.

If processor 34 determines that not all of the determined volume has been delivered ("NO" branch of block 236), processor 34 may continue delivering the fluid according to the original drug delivery schedule. In this manner, processor 34 may continue the prescribed drug delivery schedule for the first fluid and patient 1 until the next fluid (the second fluid) is ready to be delivered to patient 1. If processor 34 determines that the determined volume has been delivered ("YES" branch of block 236), processor 34 may switch to the drug delivery schedule for the second fluid and continue fluid delivery according to the schedule (238). In some examples, processor 34 may switch to a different drug delivery schedule. In other examples, processor 34 may switch to a different portion of the same drug delivery schedule specified for the second fluid. Although the example of FIG. 11 describes tracking volume of the first fluid delivered before switching to the drug delivery schedule of the second fluid, processor 34 may track time of fluid delivery in other examples to achieve similar results in maintaining the drug delivery schedule until the second fluid is delivered to patient 1.

The example of FIG. 11 is directed switching between drug delivery schedules for a first and second fluid without flow rates determined for the mixed fluid between the first and second fluid. This approach may be appropriate for situations in which little to no mixing occurs and/or the patient may not be sensitive to deviations in total drug dosing from receiving the mixed fluid. However, FIG. 11 can be modified to include an intermediate step where processor 34 switches to one or more flow rates for the mixed fluid or switches to a drug delivery schedule (e.g., a schedule including two or more flow rates at specified times) specified for the mixed fluid. In some examples, the drug delivery schedule for the mixed fluid may vary according to the changing concentration of the mixed fluid as the mixed fluid is expelled from catheter 14. In other words, processor 34 may control, according to the drug delivery schedule, the flow rate of the mixed fluid to vary as the mixed fluid is delivered to the patient in accordance to the concentrations of the mixed fluid delivered to the patient at that specific point in time. Processor 34 may thus employ a drug delivery schedule (e.g., flexible schedule) for the first fluid, the mixed fluid, and/or the second fluid throughout the transition between fluids. Processor 34 may change schedules for each fluid according to tracking time of delivery or monitoring the volume of delivered fluid.

As described herein the mixed fluid, or third fluid, may be delivered via one or more flow rates. In some examples, these flow rates may be specified by patterns and steps of a drug delivery schedule. Programmer 20, IMD 12, or any other device described herein may calculate or determine a drug delivery schedule for the mixed fluid based on the drug delivery schedules of the first and second fluids. For example, processor 50 of programmer 20 may extend the drug delivery schedules for the first and second fluids over the period of time in which the mixed fluid would be delivered to patient 1. In other words, the mixed fluid delivery would be defined by two overlapping drug delivery schedules since therapeutic agent from each fluid is present within the mixed fluid. The mixed fluid delivery may be calculated according to the respective drug delivery schedules of the first and second fluids and the concentration profile of the mixed fluid. This calculation may be done in real time as the respective drug delivery schedules progress or pre-determined and stored as a separate drug delivery schedule for the mixed fluid.

However, processor 50 may not use the flow rates specified within each schedule for the mixed fluid. Instead, processor 50 may apply a ratio or percentage to each respective flow rates to determine fractional flow rates and accommodate for the changing concentration of each therapeutic agent, which may be determined based on the concentration profile. Processor 50 may then add each fractional flow rate together to determine the overall flow rate of the mixed fluid at that time. For example, if the first fluid schedule determines a flow rate of 0.4 mL/hr for a time period and the therapeutic agent concentration of the first fluid at that time period is approximately 75 percent of the full concentration, processor 50 may calculate a first fractional flow rate of 0.3 mL/hr. If the second fluid schedule determines a flow rate of 0.2 mL/hr for the same time period and the therapeutic agent concentration of the second fluid at that time period is approximately 25 percent of the full concentration, processor 50 may calculate a second fractional flow rate of 0.05 mL/hr. Processor 50 may then calculate the flow rate for the mixed fluid and the time period to be 0.35 mL/hr and add it to the drug delivery schedule of the mixed fluid. Processor 50 may perform these calculations for the entire volume, and time of delivery, of the mixed fluid to generate various patterns of steps that effectively combine the drug delivery schedules for both the first and second fluids. Processor 50 may use predetermined time periods to perform these flow rate calculations or use the patterns and steps of the drug delivery schedules to define each time period for which to calculate a respective mixed fluid flow rate. In other examples, processor 50 may use other factors to adjust the flow rates of the mixed fluid, such as unsymmetrical concentration profiles, sensitivity of the patient to one or more of the therapeutic agents, one or more sensors that provide real-time factors related to the mixing of fluids (e.g., viscosities, temperatures, flow rates, etc.), or any other factors to generate the drug delivery schedule of the mixed fluid.

Figure 12:
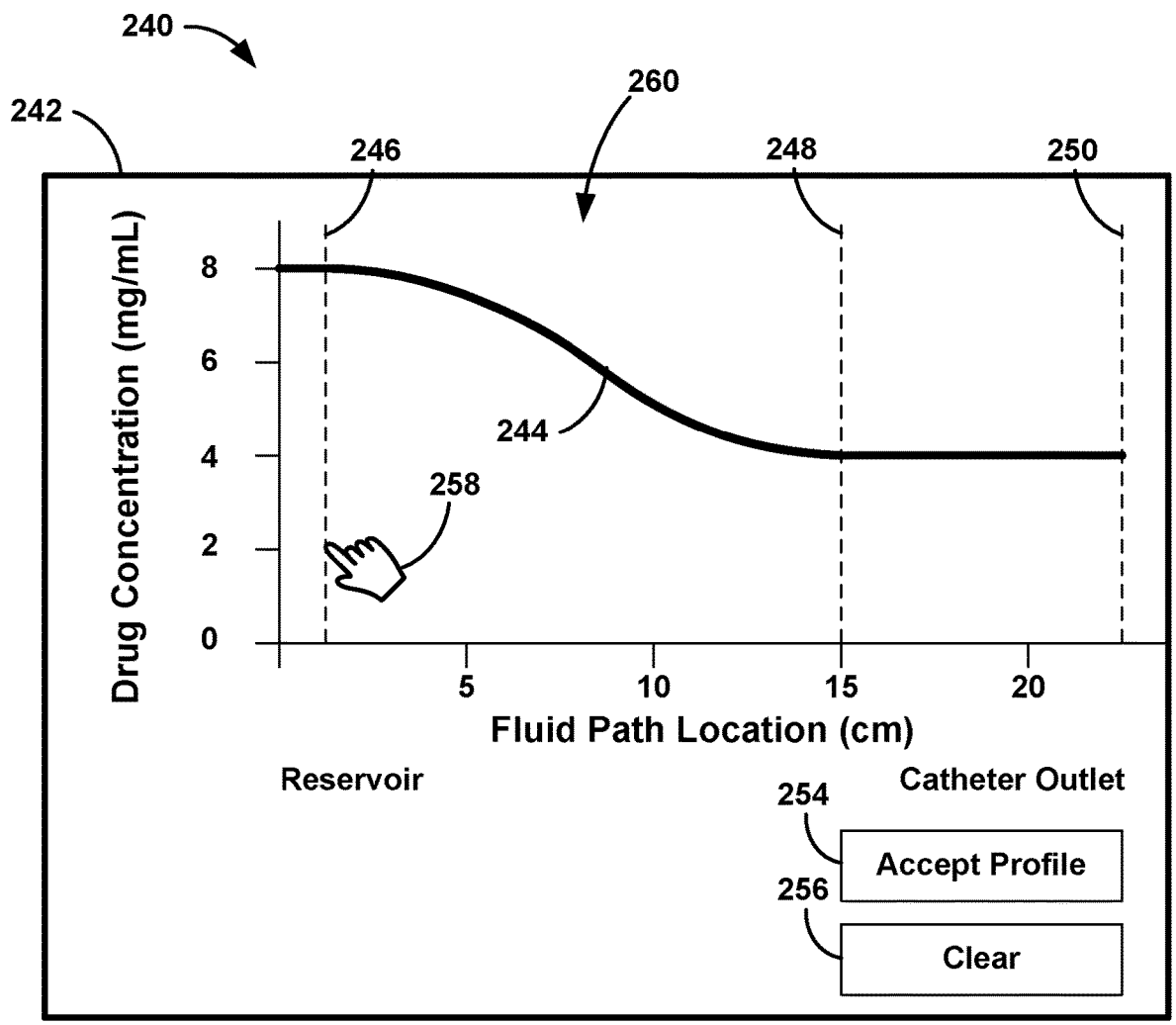
FIG. 12 is a conceptual diagram of an example user interface for receiving input regarding a concentration profile of a therapeutic agent.

FIG. 12 is a conceptual diagram of example user interface 240 for receiving input regarding concentration profile 244 of a therapeutic agent. Programmer 20 may present user interface 240 (e.g., an example of user interface 58) to a user via output device 60 and input device 62 and processor 50 may perform the various tasks described herein. As shown in FIG. 12, a user (e.g., a clinician or patient) may interact with user interface 240 to define concentration profile 244 or otherwise adjust the volume and/or time that the mixed fluid will be delivered to patient 1. Screen 242 of user interface 240 may include adjustment field 260 within which input may be received using input pointer 258 (e.g., a pointer shaped like a hand). In some examples, user interface 242 may utilize a touch screen such that the user may use a finger to directly touch and move various features of the user interface. In other examples, user interface 240 may include one or more scroll wheels, increment and decrement buttons, numerical input fields, arrows, touch pads, or any other input capable of adjusting any of the variables related to concentration profile 244 that can be adjusted by the user.

Adjustment field 260 may show concentration profile 244 for a therapeutic agent within first, second, and third fluids. Location 246 may indicate the location at which the full concentration of the second fluid meets a portion of the mixed fluid located between locations 246 and 248. Location 248 may indicate the location at which the full concentration of the first fluid meets a portion of the mixed fluid. Location 250 indicates the outlet of the catheter. If locations 246 and 248 and the concentrations of the first and second fluids are deemed accurate by the user, the user may choose to accept concentration profile 244 by selecting accept profile button 254. Accept profile button 254 may thus be input confirming the presented variables of concentration profile 244. Otherwise, the user may use input pointer 258 to select one or more areas within adjustment field 260 to change concentration profile 244.

For example, the user may move one or both of locations 246 and 248 to adjust the volume of mixed fluid that will result from the interface between the first and second fluids. The user may select location 246, for example, and move location 246 left or right to a different location within adjustment field 260. In response to receiving an input moving a location 246 or 248, processor 50 may update the shape and location of concentration profile 244. For example, moving locations 246 and 248 closer together may cause the concentration profile to have a steeper rate of change. In addition, the user may adjust the concentrations of the first and second fluids to match the concentrations to be delivered to the patient. The user may use input pointer 258 to select the portion of concentration profile 244 left of location 246 and/or the portion of concentration profile 244 between locations 248 and 250 to increase or decrease the concentrations of the first or second fluids. In response to receiving this concentration input, processor 50 may update the location and shape of concentration profile 244. In some examples, the user may move the entire concentration profile up or down or left or right within adjustment field 260 by selecting the portion of concentration profile 244 between locations 246 and 248.

In this manner, all of these areas within adjustment field 260 may be dragged to new locations in order to adjust concentration profile 244. In response to receiving a confirmation input from user selection of accept profile button 254, processor 50 may store the updated concentration profile 244 in memory and use it to perform any calculations described herein. If the user wants to start over in user interface 240, the user may select clear button 256 to bring back the default concentration profile. The initial shape of concentration profile 244 may be determined by a default stored in programmer 20.

The following examples illustrate example methods, devices, and systems described herein. Example 1: a method comprising obtaining, by one or more processors, one or more first fluid delivery parameters that at least partially define delivery of a first fluid within a downstream portion of a fluid path of a fluid delivery system, wherein a medical pump and a catheter of the fluid delivery system define at least a portion of the fluid path, obtaining, by the one or more processors, one or more second fluid delivery parameters that at least partially define delivery of a second fluid within an upstream portion of the fluid path upstream from the first fluid, wherein the second fluid comprises a therapeutic agent, determining, by the one or more processors and based on the one or more first fluid delivery parameters and the one or more second fluid delivery parameters, one or more third fluid delivery parameters that at least partially define delivery of a third fluid located between the first fluid and the second fluid in the fluid path, wherein the third fluid comprises a mixture of the first fluid and the second fluid, and wherein at least some of the one or more third fluid delivery parameters are different than the one or more first and second fluid delivery parameters, and outputting, by the one or more processors, the one or more third fluid delivery parameters for controlling the medical pump to deliver the third fluid to a patient.

Example 2: the method of example 1, wherein determining the one or more third fluid delivery parameters comprises calculating at least one of a volume, a duration, and a flow rate for delivering the third fluid to the patient.

Example 3: the method of any of examples 1 through 2, wherein obtaining the one or more first fluid delivery parameters comprises obtaining at least one of a first concentration of the first fluid, a first flow rate of the first fluid, and a first volume of the first fluid, and obtaining the one or more second fluid delivery parameters comprises obtaining at least one of a second concentration of the second fluid, a second flow rate of the second fluid, and a second volume of the second fluid.

Example 4: the method of any of examples 1 through 3, wherein obtaining the one or more first fluid delivery parameters comprises obtaining a first volume of the first fluid and a first flow rate of the first fluid, and wherein the method further comprises calculating, based on the first volume and the first flow rate, a first period of time required to deliver the first fluid to the patient at the first flow rate, determining, based on at least one of the first fluid delivery parameters and the second fluid delivery parameters, a second volume of the third fluid, determining, based on at least one of the one or more first fluid delivery parameters and the one or more second fluid delivery parameters, a second flow rate for delivering the third fluid to the patient, and determining, based on the second volume and the second flow rate, a second period of time required to deliver the third fluid out of the catheter, wherein the one or more third fluid delivery parameters comprise the second flow rate and the second period of time.

Example 5: the method of example 4, further comprising controlling the medical pump to deliver the first fluid at the first flow rate for the first period of time, responsive to the first period of time elapsing, controlling the medical pump to deliver the third fluid at the second flow rate for the second period of time, and responsive to the second period of time elapsing, controlling the medical pump to deliver the second fluid at a third flow rate, wherein each of the first flow rate, the second flow rate, and the third flow rate are different flow rates.

Example 6: the method of any of examples 1 through 5, further comprising obtaining a concentration profile of a mixture of the first fluid and a second fluid, wherein the concentration profile comprises an estimation of a change in concentration of the agent throughout the mixture, obtaining the one or more first fluid delivery parameters comprises determining, based on the concentration profile and a dimension of the fluid path, the volume of the first fluid, and determining the one or more third fluid delivery parameters comprises determining, based on the concentration profile and the dimension of the fluid path, the volume of the third fluid.

Example 7: the method of example 6, wherein obtaining the one or more first fluid delivery parameters comprises receiving a drug delivery schedule for delivering the first fluid to the patient according to one or more scheduled sets of a delivery period and a flow rate; and wherein the method further comprises calculating, based on the volume of the first fluid and the one or more sets of the delivery period and the flow rate, a first period of time for delivering the first fluid to the patient.

Example 8: the method of any of examples 1 through 8, wherein determining the one or more third fluid delivery parameters comprises determining a third flow rate for delivering the third fluid to the patient, the third flow rate having a value between values of a first flow rate of the first fluid and a second flow rate for the second fluid.

Example 9: the method of example 8, wherein determining the third flow rate comprises determining a plurality of flow rates for delivering the third fluid to the patient, and wherein the third flow rate is a selected one of the plurality of flow rates, and the plurality of flow rates are selected according to different portions of a concentration profile of a mixture of the first fluid and the second fluid.

Example 10: the method of any of examples 1 through 9, wherein one of the first fluid or the second fluid comprises an inert fluid that does not provide therapy to the patient.

Example 11: the method of any of examples 1 through 9, wherein the first fluid comprises a first concentration of the therapeutic agent, and wherein the second fluid comprises a second concentration of the therapeutic agent, wherein the second concentration is different from the first concentration.

Example 12: the method of any of examples 1 through 9, wherein the therapeutic agent is a second therapeutic agent, and wherein the first fluid comprises a first therapeutic agent different from the second therapeutic agent of the second fluid.

Example 13: the method of any of examples 1 through 12, wherein the medical pump is housed within an implantable medical device, and wherein the implantable medical device comprises the one or more processors.

Example 14: the method of any of examples 1 through 12, wherein the medical pump is housed within an external drug pump, and wherein the external drug pump comprises the one or more processors.

Example 15: a device comprising one or more processors configured to obtain one or more first fluid delivery parameters that at least partially define delivery of a first fluid within a downstream portion of a fluid path of a fluid delivery system, wherein a medical pump and a catheter of the fluid delivery system define at least a portion of the fluid path, obtain one or more second fluid delivery parameters that at least partially define delivery of a second fluid within an upstream portion of the fluid path upstream from the first fluid, wherein the second fluid comprises a therapeutic agent, determine, based on the one or more first fluid delivery parameters and the one or more second fluid delivery parameters, one or more third fluid delivery parameters that at least partially define delivery of a third fluid located between the first fluid and the second fluid in the fluid path, wherein the third fluid comprises a mixture of the first fluid and the second fluid, and wherein at least some of the one or more third fluid delivery parameters are different than the one or more first and second fluid delivery parameters, and output the one or more third fluid delivery parameters for controlling the medical pump to deliver the third fluid to a patient.

Example 16: the device of example 15, wherein the one or more processors are configured to determine the one or more third fluid delivery parameters by calculating at least one of a volume, a duration, and a flow rate for delivering the third fluid to the patient.

Example 17: the device of any of examples 15 through 16, wherein the one or more processors are configured to obtain the one or more first fluid delivery parameters by obtaining at least one of a first concentration of the first fluid, a first flow rate of the first fluid, and a first volume of the first fluid, and obtain the one or more second fluid delivery parameters by obtaining at least one of a second concentration of the second fluid, a second flow rate of the second fluid, and a second volume of the second fluid.

Example 18: the device of any of examples 15 through 17, wherein the one or more processors are configured to obtain the one or more first fluid delivery parameters by obtaining a first volume of the first fluid and a first flow rate of the first fluid, calculate, based on the first volume and the first flow rate, a first period of time required to deliver the first fluid to the patient at the first flow rate, determine, based on at least one of the first fluid delivery parameters and the second fluid delivery parameters, a second volume of the third fluid, determine, based on at least one of the one or more first fluid delivery parameters and the one or more second fluid delivery parameters, a second flow rate for delivering the third fluid to the patient, and determine, based on the second volume and the second flow rate, a second period of time required to deliver the third fluid out of the catheter, wherein the one or more third fluid delivery parameters comprise the second flow rate and the second period of time.

Example 19: the device of example 18, wherein the one or more processors are configured to control the medical pump to deliver the first fluid at the first flow rate for the first period of time, responsive to the first period of time elapsing, control the medical pump to deliver the third fluid at the second flow rate for the second period of time, and responsive to the second period of time elapsing, control the medical pump to deliver the second fluid at a third flow rate, wherein each of the first flow rate, the second flow rate, and the third flow rate are different flow rates.

Example 20: the device of any of examples 15 through 19, wherein the one or more processors are configured to obtain a concentration profile of a mixture of the first fluid and a second fluid, the concentration profile comprises an estimation of a change in concentration of the agent throughout the mixture, the one or more processors are configured to obtain the one or more first fluid delivery parameters by determining, based on the concentration profile and a dimension of the fluid path, the volume of the first fluid, and the one or more processors are configured to determine the one or more third fluid delivery parameters by determining, based on the concentration profile and the dimension of the fluid path, the volume of the third fluid.

Example 21: the device of example 20, wherein the one or more processors are configured to obtain the one or more first fluid delivery parameters by receiving a drug delivery schedule for delivering the first fluid to the patient according to one or more scheduled sets of a delivery period and a flow rate, and calculate, based on the volume of the first fluid and the one or more sets of the delivery period and the flow rate, a first period of time for delivering the first fluid to the patient.

Example 22: the device of any of examples 15 through 21, wherein the one or more processors are configured to determine the one or more third fluid delivery parameters by determining a third flow rate for delivering the third fluid to the patient, the third flow rate having a value between values of a first flow rate of the first fluid and a second flow rate for the second fluid.

Example 23: the device of example 22, wherein the one or more processors are configured to determine the third flow rate by determining a plurality of flow rates for delivering the third fluid to the patient, and wherein the third flow rate is a selected one of the plurality of flow rates, and the plurality of flow rates are selected according to different portions of a concentration profile of a mixture of the first fluid and the second fluid.

Example 24: the device of any of examples 15 through 23, wherein one of the first fluid and the second fluid comprises an inert fluid that does not provide therapy to the patient.

Example 25: the device of any of examples 15 through 23, wherein the first fluid comprises a first concentration of the therapeutic agent, and wherein the second fluid comprises a second concentration of the therapeutic agent, wherein the second concentration is different from the first concentration.

Example 26: the device of any of examples 15 through 23, wherein the therapeutic agent is a second therapeutic agent, and wherein the first fluid comprises a first therapeutic agent different from the second therapeutic agent of the second fluid.

Example 27: the device of any of examples 15 through 26, further comprising the medical pump.

Example 28: the device of any of examples 15 through 27, wherein the device is one of an implantable medical device or an external drug pump.

Example 29: the device of any of examples 15 through 28, wherein the device comprises an external programmer.

Example 30: a system comprising means for obtaining one or more first fluid delivery parameters that at least partially define delivery of a first fluid within a downstream portion of a fluid path of a fluid delivery system, wherein a medical pump and a catheter of the fluid delivery system define at least a portion of the fluid path, means for obtaining one or more second fluid delivery parameters that at least partially define delivery of a second fluid within an upstream portion of the fluid path upstream from the first fluid, wherein the second fluid comprises a therapeutic agent, means for determining, based on the one or more first fluid delivery parameters and the one or more second fluid delivery parameters, one or more third fluid delivery parameters that at least partially define delivery of a third fluid located between the first fluid and the second fluid in the fluid path, wherein the third fluid comprises a mixture of the first fluid and the second fluid, and wherein at least some of the one or more third fluid delivery parameters are different than the one or more first and second fluid delivery parameters, and means for outputting the one or more third fluid delivery parameters for controlling the medical pump to deliver the third fluid to a patient.

Example 31: a method comprising obtaining, by one or more processors, a fluid delivery schedule that defines delivery of a first fluid within a downstream portion of a fluid path of a fluid delivery system, wherein a medical pump and a catheter of the fluid delivery system define at least a portion of the fluid path, and wherein the fluid delivery schedule comprises a plurality of different patterns defining delivery of the first fluid at respective times, tracking, by the one or more processors, a location of a second fluid upstream from the first fluid in the fluid path, wherein the second fluid is different from the first fluid, and controlling, by the one or more processors and based on tracking the location of the second fluid, the medical pump to deliver the first fluid according to the fluid delivery schedule until the second fluid reaches an outlet of the catheter.

Example 32: the method of example 31, wherein the fluid delivery schedule is a first fluid delivery schedule and the plurality of different patterns is a first plurality of different patterns, and wherein the method further comprises, responsive to determining that the second fluid reaches the output of the catheter, controlling the medical pump to deliver the second fluid according to a second fluid delivery schedule different from the first fluid delivery schedule, wherein the second fluid delivery schedule comprises a second plurality of different patterns defining delivery of the second fluid at respective times.

Example 33: a system configured to perform the method of any of examples 31 and 32.

Example 34: a method comprising obtaining, by one or more processors, a first fluid delivery schedule that defines delivery of a first fluid within a downstream portion of a fluid path of a fluid delivery system, wherein a medical pump and a catheter of the fluid delivery system define at least a portion of the fluid path, and wherein the first fluid delivery schedule comprises a first plurality of different patterns defining delivery of the first fluid at respective times, obtaining, by the one or more processors, a second fluid delivery schedule that defines delivery of a second fluid upstream from the first fluid, wherein the second fluid delivery schedule comprises a second plurality of different patterns defining delivery of the second fluid at respective times, obtaining, by the one or more processors, a concentration profile of a third fluid comprising a mixture of the first fluid and a second fluid, wherein the third fluid is located between the first fluid and the second fluid, and wherein the concentration profile comprises an estimation of a change in concentration of the first fluid and the second fluid throughout the mixture of the third fluid, and determining, by the one or more processors, a third fluid delivery schedule for the third fluid based on the first fluid delivery schedule, the second fluid delivery schedule, and the concentration profile.

Example 35: the method of example 34, further comprising controlling the medical pump to deliver the third fluid according to the third fluid delivery schedule.

Example 36: the method of any of examples 34 through 35, wherein determining the third fluid delivery schedule comprises calculating, according to the first fluid delivery schedule and concentration changes of the first fluid over time defined by the concentration profile, a first partial flow rate schedule for a period of time in which the third fluid is delivered, calculating, according to the second fluid delivery schedule and concentration changes of the second fluid over time defined by the concentration profile, a second partial flow rate schedule for the period of time in which the third fluid is delivered, and adding the first partial flow rate schedule to the second partial flow rate schedule to determine a total flow rate schedule for the third fluid.

Example 37: the method of any of examples 34 through 36, further comprising controlling the medical pump to deliver the first fluid according to the first fluid delivery schedule until the third fluid reaches an outlet of the catheter, responsive to determining that the third fluid reaches the outlet of the catheter, controlling the medical pump to deliver the third fluid according to the third fluid delivery schedule until the second fluid reaches the outlet of the catheter, and, responsive to determining that the second fluid reaches the outlet of the catheter, controlling the medical pump to deliver the second fluid according to the second fluid delivery schedule.

Example 38: a system configured to perform the method of any of examples 34 through 37.

The disclosure contemplates computer-readable storage media comprising instructions to cause a processor to perform any of the functions and techniques described herein and/or any data that would be stored as described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to IMD 12 and programmer 20, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between programmer 20, IMD 12, and/or external drug pump 26. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method comprising:
controlling, by one or more processors, a medical pump of a fluid delivery system to deliver a first fluid out of an outlet of a fluid path at a first flow rate according to a first drug delivery schedule, wherein the medical pump and a catheter of the fluid delivery system define at least a portion of the fluid path;
controlling, by the one or more processors, the medical pump to deliver a second fluid out of the outlet of the fluid path at a second flow rate according to a second drug delivery schedule after delivery of the first fluid according to the first drug delivery schedule, wherein the second fluid comprises a therapeutic agent;
determining, by the one or more processors and based on at least the first drug delivery schedule of the first fluid, a third flow rate of a mixed fluid located between the first fluid and the second fluid in the fluid path, wherein the mixed fluid comprises a mixture of the first fluid and the second fluid; and
controlling, by the one or more processors, the medical pump to deliver the mixed fluid out of the outlet of the fluid path according to the third flow rate.

2. The method of claim 1, wherein determining the third flow rate of the mixed fluid comprises determining the third flow rate based on the first drug delivery schedule and the second drug delivery schedule.

3. The method of claim 1, wherein determining the third flow rate of the mixed fluid comprises calculating, based on the first drug delivery schedule and the second drug delivery schedule, a plurality of flow rates that define delivery of the mixed fluid at respective periods of time; and wherein controlling the medical pump to deliver the mixed fluid comprises controlling the medical pump to deliver the mixed fluid out of the outlet of the fluid path according to the plurality of flow rates at the respective periods of time.

4. The method of claim 3, wherein calculating the plurality of flow rates that define delivery of the mixed fluid at respective periods of time comprises determining the plurality of flow rates according to changes in a concentration profile of the mixed fluid as the mixed fluid is delivered from the outlet of the fluid path.

5. The method of claim 3, further comprising obtaining a concentration profile of the mixed fluid that comprises the mixture of the first fluid and a second fluid, wherein:

the concentration profile comprises an estimation of a change in concentration of the agent throughout the mixed fluid; and determining the plurality of flow rates that define delivery of the mixed fluid at respective periods comprises determining the plurality of flow rates to deliver a greater dosage of one of the first fluid or the second fluid than indicated by the concentration profile of the mixed fluid to err on a side of one of underdosing or overdosing during delivery of the mixed fluid out of the outlet of the fluid path.

6. The method of claim 1, wherein determining the third flow rate comprises determining the third flow rate to have a value between values of the first flow rate of the first fluid and the second flow rate for the second fluid.

7. The method of claim 1, wherein determining the third flow rate comprises determining a plurality of flow rates for delivering the mixed fluid to the patient, and wherein:

the third flow rate is a selected one of the plurality of flow rates, the plurality of flow rates are selected according to different portions of a concentration profile of the mixed fluid comprising the mixture of the first fluid and the second fluid, and controlling the medical pump to deliver the mixed fluid comprises controlling the medical pump to change between the plurality of flow rates to deliver the mixed fluid out of the outlet of the fluid path.

8. The method of claim 7, wherein controlling medical pump to change between the plurality of flow rates comprises controlling the medical pump to change between the plurality of flow rates with at least two stepped changes in flow rate.

9. The method of claim 7, wherein controlling medical pump to change between the plurality of flow rates comprises controlling the medical pump to change between the plurality of flow rates with a continuous change in flow rate.

10. The method of claim 1, wherein the therapeutic agent is a second therapeutic agent, and wherein the first fluid comprises a first therapeutic agent different from the second therapeutic agent of the second fluid.

11. The method of claim 1, further comprising:

tracking at least one of a duration the mixed fluid is delivered or a volume of the mixed fluid delivered during a transition period in which the mixed fluid is delivered between delivery of the first fluid and the second fluid;

determining that an unscheduled change to the one or more flow rates for delivery of the mixed fluid occurred during the transition period;

adjusting, to compensate for the unscheduled change, at least one of: the third flow rate of the mixed fluid to at least one adjusted flow rate for the mixed fluid, or the second flow rate of the second fluid; and controlling the medical pump to deliver at least one of the mixed fluid or the second fluid according to the at least one adjusted flow rate or the adjusted second flow rate of the second fluid.

12. A fluid delivery system, the system comprising:

a medical pump configured to deliver fluid out of a fluid path of the fluid delivery system; and one or more processors configured to:

control the medical pump of a fluid delivery system to deliver a first fluid out of an outlet of a fluid path at a first flow rate according to a first drug delivery schedule, wherein the medical pump and a catheter of the fluid delivery system define at least a portion of the fluid path;

control the medical pump to deliver a second fluid out of the outlet of the fluid path at a second flow rate according to a second drug delivery schedule after delivery of the first fluid according to the first drug delivery schedule, wherein the second fluid comprises a therapeutic agent;

determine, based on at least the first drug delivery schedule of the first fluid, a third flow rate of a mixed fluid located between the first fluid and the second fluid in the fluid path, wherein the mixed fluid comprises a mixture of the first fluid and the second fluid; and control the medical pump to deliver the mixed fluid out of the outlet of the fluid path according to the third flow rate.

13. The system of claim 12, wherein the one or more processors are configured to determine the third flow rate of the mixed fluid by determining the third flow rate based on the first drug delivery schedule and the second drug delivery schedule.

14. The system of claim 12, wherein the one or more processors are configured to determine the third flow rate of the mixed fluid by calculating, based on the first drug delivery schedule and the second drug delivery schedule, a plurality of flow rates that define delivery of the mixed fluid at respective periods of time control the medical pump to deliver the mixed fluid by controlling the medical pump to deliver the mixed fluid out of the outlet of the fluid path according to the plurality of flow rates at the respective periods of time.

15. The system of claim 14, wherein the one or more processors are configured to calculate the plurality of flow rates that define delivery of the mixed fluid at respective periods of time by determining the plurality of flow rates according to changes in a concentration profile of the mixed fluid as the mixed fluid is delivered from the outlet of the fluid path.

16. The system of claim 12, wherein:

the one or more processors are configured to obtain a concentration profile of the mixed fluid that comprises the mixture of the first fluid and a second fluid;

the concentration profile comprises an estimation of a change in concentration of the agent throughout the mixed fluid;

and
the one or more processors are configured to determine the plurality of flow rates that define delivery of the mixed fluid at respective periods by determining the plurality of flow rates to deliver a greater dosage of one of the first fluid or the second fluid than indicated by the concentration profile of the mixed fluid to err on a side of one of underdosing or overdosing during delivery of the mixed fluid out of the outlet.

17. The system of claim 12, wherein the one or more processors are configured to determine the third flow rate by determining the third flow rate to have a value between values of the first flow rate of the first fluid and the second flow rate for the second fluid.

18. The system of claim 12, wherein the one or more processors are configured to determine the third flow rate by determining a plurality of flow rates for delivering the mixed fluid to the patient, and wherein:
the third flow rate is a selected one of the plurality of flow rates,
the plurality of flow rates are selected according to different portions of a concentration profile of the mixed fluid comprising the mixture of the first fluid and the second fluid, and
the one or more processors are configured to control the medical pump to deliver the mixed fluid by controlling the medical pump to change between the plurality of flow rates to deliver the mixed fluid out of the outlet of the fluid path via at least one of at least two stepped changed in flow rate or a continuous change in flow rate.

19. The system of claim 12, wherein the one or more processors are further configured to:
track at least one of a duration the mixed fluid is delivered or a volume of the mixed fluid delivered during a transition period in which the mixed fluid is delivered between delivery of the first fluid and the second fluid;
determine that an unscheduled change to the one or more flow rates for delivery of the mixed fluid occurred during the transition period;
adjust, to compensate for the unscheduled change, at least one of: the third flow rate of the mixed fluid to at least one adjusted flow rate for the mixed fluid, or the second flow rate of the second fluid; and
control the medical pump to deliver at least one of the mixed fluid or the second fluid according to the at least one adjusted flow rate or the adjusted second flow rate of the second fluid.

20. A computer-readable storage medium comprising instructions that, when executed, cause one or more processors to:
control a medical pump of a fluid delivery system to deliver a first fluid out of an outlet of a fluid path at a first flow rate according to a first drug delivery schedule, wherein the medical pump and a catheter of the fluid delivery system define at least a portion of the fluid path;
control the medical pump to deliver a second fluid out of the outlet of the fluid path at a second flow rate according to a second drug delivery schedule after delivery of the first fluid according to the first drug delivery schedule, wherein the second fluid comprises a therapeutic agent;
determine, based on at least the first drug delivery schedule of the first fluid, a third flow rate of a mixed fluid located between the first fluid and the second fluid in the fluid path, wherein the mixed fluid comprises a mixture of the first fluid and the second fluid; and
control the medical pump to deliver the mixed fluid out of the outlet of the fluid path according to the third flow rate.

* * * * *